United States Patent
Lu et al.

(10) Patent No.: US 7,915,268 B2
(45) Date of Patent: Mar. 29, 2011

(54) 8-SUBSTITUTED 2-(BENZIMIDAZOLYL)PURINE DERIVATIVES FOR IMMUNOSUPPRESSION

(75) Inventors: Yingchun Lu, Kendall Park, NJ (US); Celia Kingsbury, Cream Ridge, NJ (US); Adolph Bohnstedt, Burlington, NJ (US); Michael Ohlmeyer, Plainsboro, NJ (US); Vidyadhar Paradkar, Somerville, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/867,397

(22) Filed: Oct. 4, 2007

(65) Prior Publication Data
US 2008/0085898 A1    Apr. 10, 2008

Related U.S. Application Data

(60) Provisional application No. 60/828,169, filed on Oct. 4, 2006.

(51) Int. Cl.
| | |
|---|---|
| C07D 473/32 | (2006.01) |
| A61K 31/52 | (2006.01) |
| A61P 35/02 | (2006.01) |
| A61P 35/00 | (2006.01) |
| A61P 11/06 | (2006.01) |
| A61P 17/06 | (2006.01) |
| A61P 19/02 | (2006.01) |
| C07D 405/12 | (2006.01) |
| C07D 405/14 | (2006.01) |
| C07D 403/04 | (2006.01) |

(52) U.S. Cl. ........... 514/263.2; 514/263.21; 514/263.22; 514/263.23; 514/263.24; 544/276; 544/277; 544/321; 544/323; 544/324; 544/326; 544/328; 544/332; 549/396; 549/399; 549/404

(58) Field of Classification Search ............... 514/263.2, 514/263.21, 263.22, 263.23, 263.24; 544/276, 544/277

See application file for complete search history.

(56) References Cited

U.S. PATENT DOCUMENTS

| | | | |
|---|---|---|---|
| 4,247,556 A | 1/1981 | von Bebenburg et al. | |
| 4,813,998 A | 3/1989 | Van Lommen et al. | |
| 5,493,011 A | 2/1996 | Jung et al. | |
| 5,705,625 A | 1/1998 | Civin et al. | |
| 5,916,792 A | 6/1999 | Civin et al. | |
| 6,313,129 B1 | 11/2001 | Uckun et al. | |
| 6,372,740 B1 * | 4/2002 | Murata et al. | 514/234.2 |
| 6,432,947 B1 | 8/2002 | Arnaiz et al. | |
| 6,452,005 B1 | 9/2002 | Uckun et al. | |
| 6,506,738 B1 | 1/2003 | Yu et al. | |
| 6,582,357 B2 | 6/2003 | Ouchi et al. | |
| 2004/0116435 A1 | 6/2004 | Eriksson et al. | |
| 2004/0116449 A1 | 6/2004 | Changelian | |
| 2004/0157739 A1 | 8/2004 | Ahrens et al. | |
| 2005/0032725 A1 | 2/2005 | Rao et al. | |
| 2007/0021443 A1 * | 1/2007 | Ohlmeyer et al. | 514/263.22 |
| 2007/0253896 A1 | 11/2007 | Le Brazidec et al. | |
| 2008/0085898 A1 | 4/2008 | Lu et al. | |
| 2008/0085909 A1 * | 4/2008 | Roughton et al. | 514/263.22 |
| 2008/0119496 A1 * | 5/2008 | Ohlmeyer et al. | 514/263.21 |
| 2008/0207613 A1 | 8/2008 | Styles et al. | |
| 2008/0214580 A1 * | 9/2008 | Neagu et al. | 514/263.2 |
| 2008/0220256 A1 * | 9/2008 | Bhattacharya et al. | 428/408 |
| 2008/0254029 A1 | 10/2008 | Yanni et al. | |
| 2008/0287468 A1 * | 11/2008 | Ohlmeyer et al. | 514/263.2 |
| 2009/0023723 A1 * | 1/2009 | Cole et al. | 514/234.2 |
| 2009/0069289 A1 * | 3/2009 | Neagu et al. | 514/210.21 |
| 2009/0281075 A1 | 11/2009 | Roughton et al. | |
| 2010/0130516 A1 * | 5/2010 | Eriksen et al. | 514/263.2 |

FOREIGN PATENT DOCUMENTS

| | | |
|---|---|---|
| CA | 2238689 | 5/1997 |
| DE | 2841209 | 4/1979 |
| DE | 10 2005 042742 | 3/2007 |
| EP | 0 277 384 | 8/1988 |
| EP | 0 807 629 | 11/1997 |
| EP | 1043324 | 10/2000 |
| EP | 1221444 | 7/2002 |
| JP | 07075798 | 3/1995 |
| JP | 2004 217582 | 4/2004 |
| WO | 99/41248 | 8/1999 |
| WO | 00/12089 | 3/2000 |

(Continued)

OTHER PUBLICATIONS

Cetkovic-Cvrlje et al., "Dual Targeting of Burton's Tyrosine kinase and Janus kinase 3 with Rationally Designed Inhibitors Prevents Graft-Versus-Host Disease (GVHD)," *British Journal of Haematology*, vol. 126, pp. 821-827 (2004).

Cetkovic-Cvrlje et al., "Targeting Janus kinase 3 in the treatment of leukemia and inflammatory diseases," *Arch. Immunol. Ther. Exp.*, vol. 52, pp. 69-82 (2004.).

Changelian et al., "Prevention of Organ Allograft Rejection by a Specific Janus Kinase 3 Inhibitor," *Science*, vol. 302, pp. 875-878 (2003).

(Continued)

*Primary Examiner* — Mark L Berch
(74) *Attorney, Agent, or Firm* — Ram W. Sabnis

(57) ABSTRACT

The present invention provides novel purines useful for the prevention and treatment of autoimmune diseases, inflammatory diseases, mast cell mediated disease and transplant rejection. The compounds of the general formula I shown below, in which Q is selected from the group consisting of CX and nitrogen; and A is chosen from the group consisting of alkyl, heterocyclyl, aryl, substituted alkyl, substituted heterocyclyl, substituted aryl, and halogen:

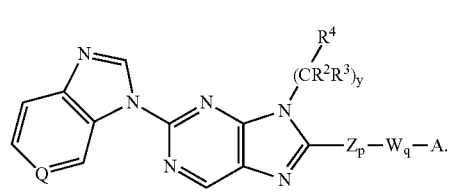

I

20 Claims, No Drawings

FOREIGN PATENT DOCUMENTS

| WO | 01/19828 | 3/2001 |
|---|---|---|
| WO | WO 02/055521 | 7/2002 |
| WO | 03/051277 | 6/2003 |
| WO | 2004/043386 | 5/2004 |
| WO | 2004/099204 | 11/2004 |
| WO | WO 2005/023761 | 3/2005 |
| WO | 2005/066156 | 7/2005 |
| WO | 2006/069080 | 6/2006 |
| WO | WO 2006/074985 | 7/2006 |
| WO | WO 2006/087538 | 8/2006 |
| WO | WO 2006/091737 | 8/2006 |
| WO | 2006/096270 | 9/2006 |
| WO | 2006/108103 | 10/2006 |
| WO | 2007/035873 | 10/2006 |
| WO | WO 2007/058990 | 5/2007 |
| WO | WO 2007/140222 | 12/2007 |
| WO | WO 2007/146712 | 12/2007 |
| WO | WO 2008/043019 | 4/2008 |
| WO | WO 2008/043031 | 4/2008 |
| WO | WO 2008/051493 | 5/2008 |
| WO | WO 2008/051494 | 5/2008 |
| WO | WO 2008/143674 | 11/2008 |
| WO | WO 2009/062059 | 5/2009 |

OTHER PUBLICATIONS

O'Shea, J.J., "Cytokine signaling: new insights and new opportunities for therapeutic intervention?", *Arthristis Res.*, vol. 3(Suppl A): L018 (2001).

Ortmann et al., "Janus kinases and signal transducers and activators of transcription: their roles in cytokine signaling, development and immunoregulation," *Arthritis Res.*, ,vol. 2, pp. 16-32 (2000).

Yamaoka et al., "The Janus kinases (Jaks)," *Genome Biology*, vol. 5:253, pp. 253.1-253.6 (2004).

Uckun et al., "Structure-based Design of Novel Anticancer Agents," *Current Cancer Drug Targets*, vol. 1(1), pp. 59-71 (2001).

Kawahara et al., "Critical role of the interleukin 2 (IL-2) receptor y-chain associated Jak3 in the IL-2-induced c-*fos* and c-*myc*, but not *bcl*-2, gene induction," *Proc. Natl. Acad. Sci.*, vol. 92, pp. 8724-8728 (1995).

O'Shea et al., "A New Modality for Immunosuppression: Targeting the Jak/Stat Pathway," *Nature Reviews*, vol. 3, pp. 555-564 (2004).

Papageorgiou et al., "Is Jak3 a new drug target for immunomodulation-based therapies?" *TRENDS in Pharmacological Sciences*, vol. 25(11), pp. 558-562 (2004).

Lin et al., "Constitutive Activation of Jak3/Stat3 in Colon Carcinoma Tumors and Cell Lines", *American Journal of Pathology*, vol. 167(4), pp. 969-980 (2005).

Dana et al, "Role of Immunity and Inflammation in Corneal and Ocular Surface Disease Associated with Dry Eye," *Lacrimal Gland, Tear Film and Dry Eye Syndromes 3*, pp. 729-738 (2002).

Nagelhout et al., "Preservation of Tear Film Integrity and Inhibition of Corneal Injury by Dexamethasone in a Rabbit Model of Lacrimal Gland Inflammation-Induced Dry Eye," *Journal of Ocular Pharmacology and Therapeutics*, vol. 21(2), pp. 139-148 (2005).

Pflugfelder, S., "Perspective Anti-inflammatory Therapy for Dry Eye," *American Journal of Ophthalmology*, vol. 137(2), pp. 337-342 (2004).

Amin et al., "Inhibition of Jak3 induces apoptosis and decreases anaplastic lymphoma kinase activity in anaplastic large cell lymphoma," *Oncogene*, vol. 22, pp. 5399-5407 (2003).

Harrington et al., "VX-680, a potent and selective small-molecule inhibitor of the Aurora kinases, suppresses tumor growth in vivo," *Nature Medicine*, vol. 10(3), pp. 262-267 (2004).

Jung et al., "Discovery of Novel and Potent Thiazoloquinazolines as Selective Aurora A and B Kinase," American Chem Soc., pp. 1-16 (2005).

Frantz, S., "Playing Dirty", *Nature*, vol. 437, pp. 942-943 (2005).

Martinez-Lostao et al., "Role of the STAT1 pathway in apoptosis induced by fludarabine and Jak kinase inhibitors in B-cell chronic lymphocytic leukemia," *Leuk Lymphoma*, vol. 46(3), pp. 435-442 (2005), Abstract only (PMID: 15621835).

Lai et al., "Jak3 activation is significantly associated with ALK expression in anaplastic large cell lymphoma," *Human Pathology*, vol. 36, pp. 939-944 (2005).

Pearson, H., "Designer transplant drug shows promise in monkeys," *News & Nature* (2003).

Goldberg et. al., "Optimization of 2-Phenylaminoimidazo [4,5-*h*]isoquinolin-9-ones: Orally Active Inhibitors of Ick Kinase," *Journal of Medical Chem.*, vol. 46, pp. 1337-1349.

International Search Report from International Application No. PCT/US2006/012824.

International Search Report from International Application No. PCT/US2006/061004.

Beijersbergen van Henegouwen GM et al., Hydrolysis of RRR0alpha-tocopheryl acetate (vitamin # acetate) in the skin and its UV protecting activity (an in vivo study with the rat) *J Photochem Photobiol*, Jul. 29, 2005, vol. 1, pp. 45-51.

International Search Report from International Application No. PCT/US2007/080447.

International Search Report from International Application No. PCT/US2007/080464.

International Search Report and Written Opinion from International Application No. PCT/US2007/081232.

International Search Report and Written Opinion from International Application No. PCT/US2007/069530.

Hirota et all, "Synthesis and Biological Evaluation of 2,8-Disubstituted 9-Benzyladenines: Discovery of 8-Mercaptoadenines as Potent Interferon-Inducers," *Bioorganic & Medicinal Chemistry 11*, 2003, pp. 2715-2722.

Written Opinion corresponding to PCT/US2007/080447.
Written Opinion corresponding to PCT/US2007/080464.
Written Opinion corresponding to PCT/US2006/012824.
Written Opinion corresponding to PCT/US2006/061004.

Cadena-Amaro et al., Synthesis and incorporation into DNA fragments of the artificial nucleobase, 2-amino-8-oxopurine, Bioorganic & Medicinal Chemistry Letters, 2005, vol. 15, Issue 4, pp. 1069-1073.

Chem Abstracts Search #1 1996:496070 CAPLUS: Bakavoli et al., Synthesis of 4, 4'-bis-pyrimidines and some related bis-fused pyrimidines, Journal of Sciences, Islamic Republic of Iran, 1995, vol. 6, Issue 3, pp. 158-162.

Chem Abstracts Search #2 1980:604652 CAPLUS: Brazilian patent No. BR 7806210, Apr. 1, 1980.

Frankowski, Synthesis of imidazo [4,5-c]pyridine and imidazo [4,5-d][1,2] diazepine systems and their ribonucleosides, Tetrahedron, 1986, vol. 42, Issue 5, pp. 1511-1528.

Gaulon et al., A General and Facile Route to New Trisubstituted Purin-8-ones, Synthesis, Jul. 2005, vol. 13, pp. 2227-2233.

International Search Report dated Jan. 9, 2007 in International Application No. PCT/US2006/036833, filed Sep. 21, 2006.

International Search Report dated Mar. 20, 2009 for International Application No. PCT/US2008/082832 filed Nov. 7, 2008.

Lum et al., 2,5-Diaminopyrimidines and 3,5-disubstituted azapurines as inhibitors of glycogen synthase kinase-3 (GSK-3), Bioorganic & Medicinal Chemistry Letters, 2008, vol. 18, Issue 12, pp. 3578-3581.

Pochet et al., Construction of a self-complementary nucleoside from deoxyguanosine, Comptes Rendus de l'Academie des Sciences, Serie III: Sciences de la Vie, 1996, vol. 319, Issue 1, pp. 1-7.

Rokos et al., 8.2-Anhydro-8-Hydroxypurine α-D-Ribosides, J. Carbohydrates, Neclosides, Nucleotides, 1976, Issue 77-91.

* cited by examiner

8-SUBSTITUTED 2-(BENZIMIDAZOLYL)PURINE DERIVATIVES FOR IMMUNOSUPPRESSION

CROSS-REFERENCE TO RELATED APPLICATIONS

This application claims priority to U.S. Provisional application Ser. No. 60/828,169 filed Oct. 4, 2006, the entire contents of which are hereby incorporated by reference.

FIELD OF THE INVENTION

The invention relates to 8-substituted 2-(benzimidazolyl) purine derivatives and 8-substituted 2-(imidazolo[4,5-c]pyridinyl)purine derivatives useful as immunosuppressants.

BACKGROUND OF THE INVENTION

Immunosuppression is an important clinical approach in treating autoimmune disease and in preventing organ and tissue rejection. The clinically available immunosuppressants, including azathioprine, cyclosporine and tacrolimus, although effective, often cause undesirable side effects including nephrotoxicity, hypertension, gastrointestinal disturbances and gum inflammation. Inhibitors of the tyrosine kinase Jak3 are known to be useful as immunosuppressants (see U.S. Pat. No. 6,313,129).

The members of the Janus kinase (Jak) family of non-receptor intracellular tyrosine kinases are components of cytokine signal transduction. Four family members have been identified to date: Jak1, Jak2, Jak3 and Tyk2. The Jaks play a key role in the intracellular signaling mediated through cytokine receptors. Upon binding of cytokines to their receptors, Jaks are activated and phosphorylate the receptors, creating docking sites for other signaling molecules, in particular members of the signal transducer and activator of transcription (STAT) family. While expression of Jak1, Jak2 and Tyk2 is relatively ubiquitous, Jak3 expression is temporally and spatially regulated. Jak3 is predominantly expressed in cells of hematopoietic lineage; it is constitutively expressed in natural killer (NK) cells and thymocytes and is inducible in T cells, B cells and myeloid cells (reviewed in Ortmann, et al., 1999 and Yamaoka, et al., 2004). Jak3 is also is expressed in mast cells, and its enzymatic activity is enhanced by IgE receptor/FcεRI cross-linking (Malaviya and Uckun, 1999).

A specific, orally active Jak3 inhibitor, CP-690,550, has been shown to act as an effective immunosuppressant and prolong animal survival in a murine model of heart transplantation and a primate model of kidney transplantation (Changelian, et al., 2003).

Furthermore, aberrant Jak3 activity has been linked to a leukemic form of cutaneous T-cell lymphoma (Sezary's syndrome) and acute lymphoblastic leukemia (ALL), the most common form of childhood cancer. The identification of Jak3 inhibitors has provided the basis for new clinical approaches in treating leukemias and lymphomas (reviewed in Uckun, et al, 2005). Two dimethoxyquinazoline derivatives, WHI-P131 (JANEX-1) and WHI-P154 (JANEX-2), have been reported to be selective inhibitors of Jak3 in leukemia cells (Sudbeck et al., 1999).

Jak3 has also been shown to play a role in mast-cell mediated allergic reactions and inflammatory diseases and serves as a target in indications such as asthma and anaphylaxis.

Therefore, compounds that inhibit Jak3 are useful for indications such as leukemias and lymphomas, organ and bone marrow transplant rejection, mast cell-mediated allergic reactions and inflammatory diseases and disorders.

SUMMARY OF THE INVENTION

It has now been found that compounds of general formula I are potent and selective inhibitors of Jak3:

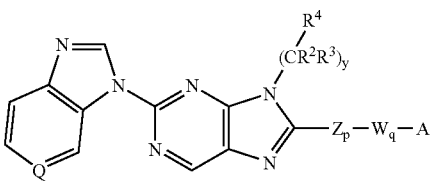

In these compounds,
Q is selected from the group consisting of CX and nitrogen;
X is selected from the group consisting of hydrogen, halogen and an electron-withdrawing group;
Z is selected from the group consisting of oxygen, sulfur, and $NR^2$;
p is zero or one;
A is chosen from the group consisting of alkyl, heterocyclyl, aryl, substituted alkyl, substituted heterocyclyl, substituted aryl, and halogen;
W is $(C_1-C_6)$alkylene;
q is zero or one;
y is zero or an integer selected from 1, 2 and 3;
$R^2$ and $R^3$ are selected independently for each occurrence from the group consisting of hydrogen and $(C_1-C_6)$alkyl;
$R^4$ is selected from the group consisting of alkyl, alkoxy, heterocyclyl, aryl, substituted alkyl, substituted heterocyclyl, substituted aryl, and $C(O)NHR^7$; and
$R^7$ is selected from the group consisting of alkyl and haloalkyl.

The members of this genus are useful in inhibiting Jak3 activity and as such are useful in indications where clinical immunosuppression is desired and in the treatment of hematological cancers.

In another aspect, the invention relates to pharmaceutical compositions comprising a therapeutically effective amount of at least one compound of general formula I, or a pharmaceutically acceptable salt thereof, and a pharmaceutically acceptable carrier.

In another aspect, the invention relates to a method for treating a disease by altering a response mediated by Jak3 tyrosine kinase. The method comprises bringing into contact with Jak3 at least one compound of general formula I.

In yet another aspect the present invention relates to a method of suppressing the immune system in a subject in need thereof comprising administering to the subject a therapeutically effective amount of at least one compound of general formula I.

Suppression of immune system activity is desirable for preventing or treating tissue or organ rejection following transplant surgery and for preventing and treating diseases and disorders arising from aberrant activity of the immune system, in particular autoimmune disorders and diseases. Exemplary autoimmune disorders include graft versus host disease (GVHD), insulin-dependent diabetes (Type I), Hashimoto's thyroiditis and Graves' disease, pernicious anemia, Addison's disease, chronic active hepatitis, Crohn's disease, ulcerative colitis, rheumatoid arthritis, multiple sclerosis, systemic lupus erythematosus, psoriasis, scleroderma and myasthenia gravis.

The compounds of the present invention are useful in preventing and treating diseases and disorders related to mast cell-mediated allergic reactions and inflammation.

Other indications in which the Jak3 inhibitors are useful include leukemias and lymphomas.

DETAILED DESCRIPTION OF THE INVENTION

Throughout this specification the substituents are defined when introduced and retain their definitions.

In a first aspect the invention relates to purines having general formula I:

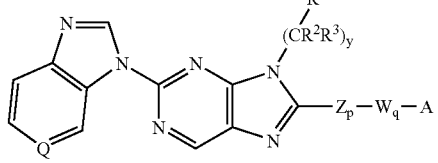

I

The members of the genus I may be conveniently divided into two subgenera based on the values of Q. When Q is nitrogen, a subgenus of purines having an attached imidazo[5,4-c]pyridine arises. When Q is carbon, a subgenus of purines having an attached benzimidazole arises. The structures of these subgenera are shown below:

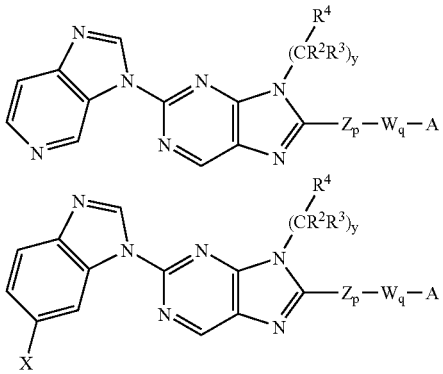

In certain embodiments, X may be hydrogen, halogen or an electron-withdrawing residue containing one or fewer carbons. For example, X may be H, F, Cl, CN, $CF_3$ or $OCF_3$. In some embodiments, y is 1 or 2 and $R^2$ and $R^3$ are hydrogen or methyl, and in particular, y may be one, both of $R^2$ and $R^3$ may be hydrogen and $R^4$ may be selected from aryl, heteroaryl and their substituted counterparts. In other embodiments, y may be one to three, $R^2$ and $R^3$ may be hydrogen in all occurrences and $R^4$ may be alkoxy.

In yet other embodiments, y is zero and $R^4$ is a residue selected from an optionally substituted monocycle or bicycle. The $R^4$ residue in this case contains at least one oxygen atom. More particularly, $R^4$ may be an oxygen heterocycle, an amide, a substituted alkyl amide, a halogen-substituted oxygen heterocycle or an alkoxy-substituted cycloalkyl, such as

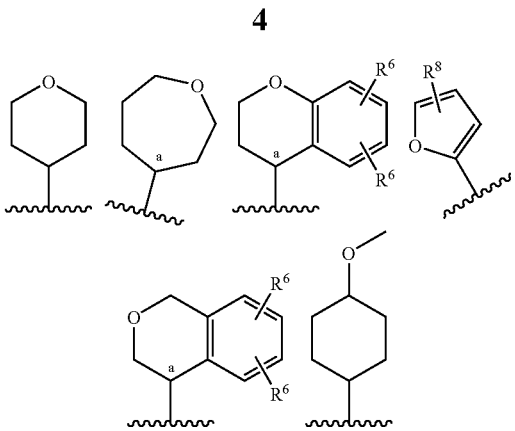

or $R^4$ may be hydroxycycloalkyl or hydroxyaryl, such as

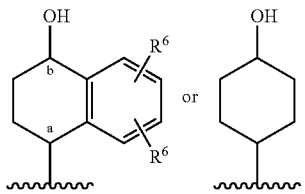

wherein $R^6$ in each occurrence is hydrogen or fluorine, $R^8$ is selected from hydrogen, lower alkyl, a halogen, and $CF_3$, and "a" and "b" represent stereogenic centers. In the above compounds, the carbon marked with an "a" may be of the (R)—absolute configuration. In the 4-hydroxy cyclohexane and fused systems such as hydroxytetralin and substituted hydroxyl tetralin, the stereogenic centers "a" and "b" are preferably trans.

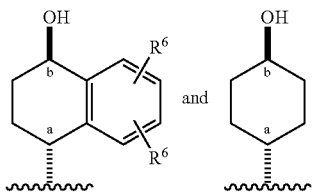

In the chroman, the carbon marked with an "a" may be of the R absolute configuration:

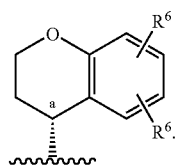

In other embodiments, p is zero and q is zero, resulting in compounds of general formula II

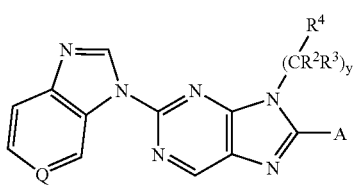

II

In yet other embodiments, A is heterocyclyl, substituted heterocyclyl, aryl, substituted aryl, $(C_1-C_6)$alkyl, substituted $(C_1-C_6)$alkyl, cyano or halogen. For example, A may be piperidinyl, morpholinyl, pyrimidinyl, methyl, pyridinyl, 2-aminopyrimidinyl, acetamidophenyl, propyl, hydroxyphenyl, carboxyphenyl, methanesulfonamidophenyl, halopyridinyl, methoxypyridinyl, methylpyridinyl, chloromethyl, furanyl, pyrrolyl, ethyl, butyl, imidazolyl, N-methylimidazolyl, phenyl, (aminosulfonyl)phenyl, (dialkylamino)pyrimidinyl, hydroxypyrimidinyl, (trifluoromethyl)pyridinyl, oxopyridinyl, (alkylthio)pyrimidinyl, (trifluoromethyl)phenyl, cyanophenyl, pyridine-N-oxide, methoxyphenyl, methylpyrrolyl, methylfuranyl, tetrahydrofuranyl, methylphenyl, cyclopentyl, thiazolyl, halophenyl, benzyl, (methoxycarbonyl)phenyl, indolyl, quinolinyl, or (trifluoromethoxy)phenyl. In another embodiment, Z is sulfur, p is one, q is zero and A is an optionally substituted alkyl, so that the substituent at the purine 8 position is methylthio.

In yet other embodiments, Q is CX, X is H, F, Cl, CN, $CF_3$ or $OCF_3$, p and q are zero, A is a heterocyclyl, substituted heterocyclyl, aryl, substituted aryl, $(C_1-C_6)$alkyl, substituted $(C_1-C_6)$alkyl or halogen, y is zero, and $R^4$ is a residue selected from an optionally substituted monocycle or bicycle containing at least one oxygen atom.

All of the compounds falling within the foregoing parent genera and their subgenera are useful as Jak3 inhibitors. It may be found upon examination that species and genera not presently excluded are not patentable to the inventors in this application. In this case, the exclusion of species and genera in applicants' claims are to be considered artifacts of patent prosecution and not reflective of the inventors' concept or description of their invention. The invention, in a composition aspect, is all compounds of formula I except those that are in the public's possession.

DEFINITIONS

For convenience and clarity certain terms employed in the specification, examples and claims are described herein.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl (both n-propyl and isopropyl), butyl (including s- and t-butyl) and the like. Preferred alkyl groups are those of $C_{20}$ or below; more preferred are $C_1-C_8$ alkyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, cyclohexyl, norbornyl and the like.

$C_1$ to $C_{20}$ hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Heteroalkyl refers to alkyl residues in which one or more carbons (and their associated hydrogens) have been replaced by a heteroatom. For example, oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and for the purposes of the present invention, fused moieties such as tetrahydronaphthalene (tetralin), indane and fluorene, in which one or more rings are aromatic, but not all need be. The 5- to 10-membered aromatic heterocyclic rings include, e.g., imidazole, pyridine, indole, indoline, thiophene, benzopyranone, thiazole, furan, benzimidazole, benzodioxole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl. A nitrogenous heterocycle is a heterocycle containing at least one nitrogen in the ring; it may contain additional nitrogens, as well as other heteroatoms.

The term "carbocycle" is intended to include ring systems, including polycyclic structures, consisting entirely of carbon but of any oxidation state. Thus $(C_3-C_{10})$ carbocycle refers to such systems as cyclopropane, benzene and cyclohexene; $(C_8-C_{12})$ carbopolycycle refers to such systems as norbornane, decalin, indane and naphthalene.

The terms "monocycle" and "bicycle" or "monocyclic" and "bicyclic" refer to carbocycles and heterocycles having one or two rings respectively. Preferred monocycles are 3, 4, 5, 6 or 7-membered rings, which may be aromatic, saturated or partially unsaturated. Non-limiting examples include cyclopropane, cyclopentane, cyclohexane, pyran, furan, tetrahydrofuran, tetrahydropyran, oxepane and phenyl. Preferred bicycles are those having from 8 to 12 ring atoms in total. Non-limiting examples include chroman, tetralin, naphthalene, benzofuran, indole, octahydropentalene and tetrahydrobenzo[b]oxepine. A particular embodiment comprises fused 5:6 and 6:6 systems.

Substituted alkyl, aryl, cycloalkyl, heterocyclyl etc. refer to alkyl, aryl, cycloalkyl, or heterocylyl wherein up to three H atoms in each residue are replaced with halogen, haloalkyl, hydroxy, loweralkoxy, hydroxyloweralkyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzenesulfonyl, benzyloxy, or heteroaryloxy. When the parent is a heterocycle that allows such substitution, the term also includes oxides, for example pyridine-N-oxide, thiopyran sulfoxide and thiopyran-S,S-dioxide. As mentioned above, two hydrogens on a single carbon may be replaced by a carbonyl to form an oxo derivative. Noteworthy oxo-substituted aryl residues include tetralone (3,4-dihydronaphthalen-1(2H)-one) and indanone (2,3-dihydroinden-1-one).

The terms "halogen" and "halo" refer to fluorine, chlorine, bromine or iodine.

The terms "electron-withdrawing group" or "electron-withdrawing residue" refer to substituents which have a Hammett σ$_{meta}$ greater than 0.2. Examples of such substituents include cyanide, trifluoromethoxy, trifluoromethyl, chlorine and fluorine.

Some of the compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as mixtures thereof, including racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E or a mixture of the two in any proportion.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. For example, the graphic representation

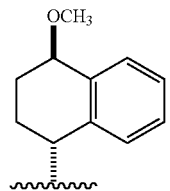

indicates either, or both, of the two trans enantiomers

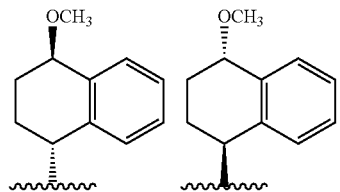

It will be recognized that the compounds of this invention can exist in radiolabeled form, i.e., the compounds may contain an unnatural ratio of one or more atoms containing an atomic mass or mass number different from the atomic mass or mass number usually found in nature. Radioisotopes of hydrogen, carbon, phosphorous, fluorine, chlorine and iodine include $^3$H, $^{14}$C, $^{35}$S, $^{18}$F, $^{36}$Cl and $^{125}$I, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples by substituting a readily available radiolabeled reagent for a non-radiolabeled reagent. Because of the high affinity for the JAK3 enzyme active site, radiolabeled compounds of the invention are useful for JAK3 assays.

An oxygenous heterocycle is a heterocycle containing at least one oxygen in the ring; it may contain additional oxygens, as well as other heteroatoms. Exemplary oxygenous heterocycles include tetrahydropyran, chroman and their variously substituted derivatives, such as:

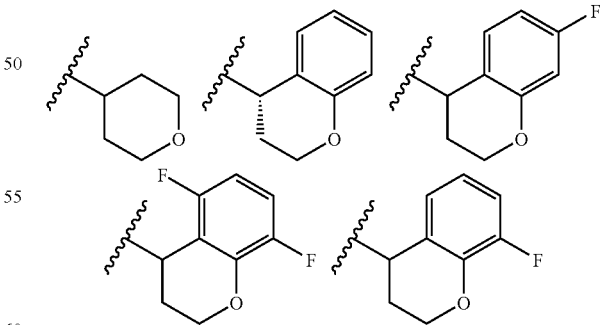

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

The present invention further provides pharmaceutical compositions comprising as active agents, the compounds described herein.

As used herein a "pharmaceutical composition" refers to a preparation of one or more of the compounds described herein, or physiologically acceptable salts or solvates thereof, with other chemical components such as physiologically suitable carriers and excipients.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Compounds that inhibit Jak-3 can be formulated as pharmaceutical compositions and administered to a mammalian subject, such as a human patient in a variety of forms adapted to the chosen route of administration, i.e., orally or parenterally, by intravenous, intramuscular, topical, transdermal or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating may be useful as it is may be desirable to prevent exposure of the compounds of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the composition. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compounds of the present invention may also be formulated in rectal compositions such as suppositories or retention enemas, using, e.g., conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound of Formula I or II in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

It should be understood that in addition to the ingredients particularly mentioned above, the formulations of this invention may include other agents conventional in the art having regard to the type of formulation in question, for example those suitable for oral administration may include flavoring agents.

The compositions may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Compositions comprising a compound of the present invention formulated in a compatible pharmaceutical carrier may also be placed in an appropriate container and labeled for treatment of an indicated condition.

Indications

The compounds of the present invention are useful in inhibiting the activity if Jak3 or in inhibiting Jak3 mediated activity and are useful as immunosuppressive agents for tissue and organ transplants, including bone marrow transplant and in the treatment of autoimmune and inflammatory diseases and of complications arising therefrom.

Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas; Hashimoto's thyroiditis and Graves' disease which affect the thyroid gland; pernicious anemia which affects the stomach; Cushing's disease and Addison's disease which affect the adrenal glands; chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting β cells of the islets of Langerhans. Targeting Jak3 in this disease is based on the observation that multiple cytokines that signal through the Jak pathway are known to participate in the T-cell mediated autoimmune destruction of β cells. Indeed, a Jak3 inhibitor, JANEX-1 was shown to prevent spontaneous autoimmune diabetes development in the NOD mouse model of type I diabetes.

Graft-versus-host disease (GVHD) is a donor T-cell initiated pathological condition that frequently follows allogeneic bone marrow transplantation (BMT). Substantial experimental and clinical research have demonstrated that donor T-cells are the principal mediators and effectors of GVHD. Jak3 plays a key role in the induction of GVHD and treatment with a Jak3 inhibitor, JANEX-1, was shown to attenuate the severity of GVHD (reviewed in Cetkovic-Cvrlje and Ucken, 2004).

Mast cells express Jak3 and Jak3 is a key regulator of the IgE mediated mast cell responses including the release of inflammatory mediators. Jak3 was shown to be a valid target in the treatment of mast cell mediated allergic reaction.

Allergic disorders associated with mast cell activation include Type I immediate hypersensitivity reactions such as allergic rhinitis (hay fever), allergic urticaria (hives), angioedema, allergic asthma and anaphylaxis, i.e., "anaphylatic shock." These disorders are treated or prevented by inhibition of Jak3 activity, for example, by administration of a Jak3 inhibitor according to the present invention.

According to the present invention, the Jak3 inhibitors may be administered prophylactically, i.e., prior to onset of acute allergic reaction, or they may be administered after onset of the reaction, or at both times.

Inflammation of tissues and organs occurs in a wide range of disorders and diseases and in certain variations results from activation of the cytokine family of receptors. Exemplary inflammatory disorders associated with activation of Jak3 include, in a non-limiting manner, skin inflammation due to radiation exposure, asthma, allergic inflammation and chronic inflammation.

The Jak3 inhibitors of the present invention are also useful in treating certain malignancies, including skin cancer and hematological malignancy such as lymphomas and leukemias.

The following examples will further describe the invention, and are used for the purposes of illustration only, and should not be considered as limiting the invention being disclosed.

EXAMPLES

The following abbreviations and terms have the indicated meaning throughout:

| | |
|---|---|
| Ac = | acetyl |
| Bu = | butyl |
| DCM = | dichloromethane = methylene chloride = $CH_2Cl_2$ |
| DEAD = | diethyl azodicarboxylate |
| DIC = | diisopropylcarbodiimide |
| DIEA = | N,N-diisopropylethyl amine |
| DMF = | N,N-dimethylformamide |
| DMSO = | dimethyl sulfoxide |
| EA (EtOAc) = | Ethyl Acetate |
| GC = | gas chromatography |
| h = | hours |
| HOAc = | acetic acid |
| HOBt = | hydroxybenzotriazole |
| Me = | methyl |
| $Pd(dppf)_2Cl_2$ = | dichloro[1,1'-bis(diphenylphosphinoferrocene] palladium |
| Ph = | phenyl |
| PhOH = | phenol |
| RT = | room temperature |
| sat'd = | saturated |
| s- = | secondary |
| t- = | tertiary |
| TBDMS = | t-butyldimethylsilyl |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

Examples below describe syntheses of certain precursors and intermediates of the invention.

Synthesis and resolution of
8-fluorochroman-4-amine

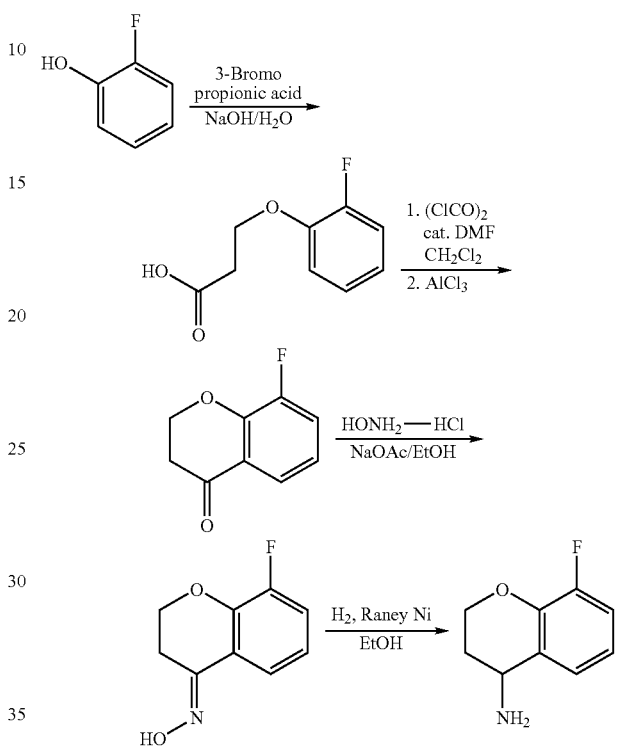

3-(2-Fluorophenoxy)propanoic acid. A mixture of 2-fluorophenol (15 g), 3-bromopropanoic acid (20 g) and NaOH (11 g) was refluxed in 50 mL of water. The solution was cooled to room temperature and acidified to pH 2 with 3 M HCl. The resulting precipitate was isolated by filtration to yield 9.27 g of title compound as a white solid. The filtrate was extracted 3 times with EtOAc to yield 2.5 g of less pure compound.

8-Fluorochroman-4-one. Oxalyl chloride (8.79 mL) and 1 drop of DMF were added to an ice cold solution of 3-(2-fluorophenoxy)propanoic acid (9.27 g) in DCM (50 mL). The solution was stirred at 0° C. for 2 hours, then aluminum chloride (7.39 g, 55.42 mM) was added and the solution was stirred for 16 hours at room temperature. The mixture was poured onto ice water, and extracted three times with DCM. The combined organics were washed with 0.5M NaOH and brine, then dried, evaporated, and purified by column chromatography (eluting with 20% EtOAc/Hex) to give of the title compound (8.20 g, 98%).

8-Fluorochroman-4-amine. A round bottom flask was charged with 8-fluorochroman-4-one (8.2 g), hydroxylamine hydrochloride (3.78 g) and sodium acetate (4.46 g). A reflux condenser was added, the flask was purged with argon, dry EtOH (20 mL) was added, and the mixture was stirred at reflux for 18 hours. The solution was cooled to room temperature, diluted with EtOAc, and washed with water. The organic phase was dried, and evaporated to give the intermediate 8-fluorochroman-4-one oxime, which was reduced with Raney Nickel in EtOH at 50 PSI to yield the titled amine (4.69 g, 57%).

Resolution of 8-fluorochroman-4-amine: (Procedure based on US published application 2004/0157739).

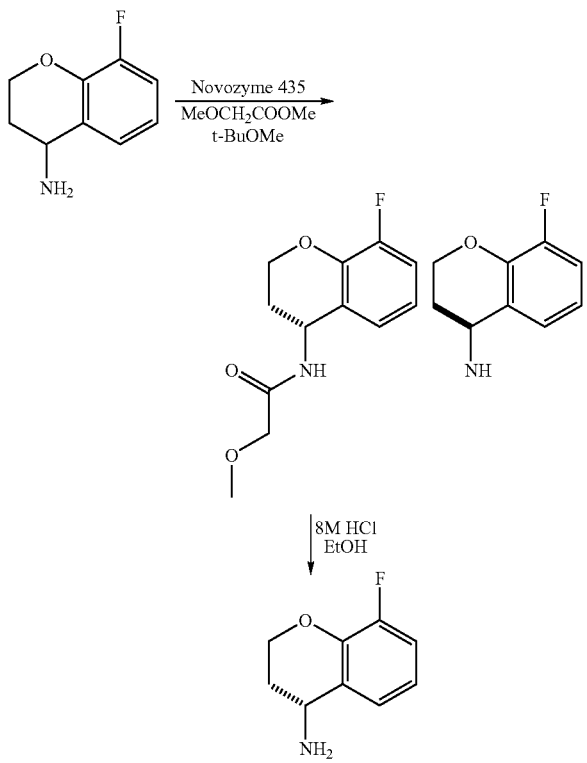

A mixture of 8-fluorochroman-4-amine (3.40 g), methyl 2-methoxyacetate (2.44 g) and Novozyme 435 (Aldrich, 0.68 g) in anhydrous tert-butyl methyl ether (75 mL) was heated at reflux under argon for 2 hours (at which time the ratio of acylated to unacylated product was 1:1 by HPLC). The solid that formed upon cooling was collected via filtration and dissolved in EtOAc. The mixture was filtered to remove the biocatalyst and washed once with 0.5M HCl to remove any lingering (S)-amine. The solvent was evaporated and the product was recrystallized from tert-butyl methyl ether to yield (R)—N-(8-fluorochroman-4-yl)-2-methoxyacetamide (0.78 g). The reaction solvent and recrystallization mother liquor was washed 3 times with 0.5 M HCl and concentrated to yield additional (R)—N-(8-fluorochroman-4-yl)-2-methoxyacetamide (0.83 g). The combined acidic aqueous layers were made basic by NaOH and extracted with DCM to yield (S)-8-fluorochroman-4-amine (1.6 g). A solution of (R)—N-(8-fluorochroman-4-yl)-2-methoxyacetamide (0.78 g) in 8M HCl in EtOH (50 mL) was heated at reflux for 4 hours. The solvents were removed from the cooled reaction mixture, the resulting solid was taken up in 50 mL of 0.5M NaOH, salted out with NaCl$_{(s)}$, and extracted 4 times with DCM to yield (R)-8-fluorochroman-4-amine (0.48 g, 87%). The % ee was checked via chiral HPLC: Chiralcel OD-H (0.46×25 cm analytical column, Daicel Chemical Industries) method: isocratic 5% (0.05% TFA/EtOH) 95% (0.05% TFA/Hex), Rt=7.2 min (S)-enantiomer, Rt=9.2 min (R)-enantiomer.

Other similar amines, such as chroman-4-amine, 5-fluorochroman-4-amine, 6-fluorochroman-4-amine, 6-chlorochroman-4-amine, 6-methylchroman-4-amine, 6-methoxychroman-4-amine, 7-fluorochroman-4-amine, 5,8-difluorochroman-4-amine, and 6,8-difluorochroman-4-amine, were prepared via procedures described above for the synthesis of 8-fluorochroman-4-amine. The corresponding chroman-4-ones were commercially available as advanced intermediates for the synthesis of chroman-4-amine, 6-fluorochroman-4-amine, 6-chlorochroman-4-amine, 6-methylchroman-4-amine, and 6-methoxychroman-4-amine. For the synthesis of 5-fluorochroman-4-amine, the intermediate 5-fluorochroman-4-one was obtained using procedures from GB 2355264, which also provided 7-fluorochroman-4-one. 7-Fluorochroman-4-one could be used in the synthesis of 7-fluorochroman-4-amine. Chroman-4-amine, 5-fluorochroman-4-amine, 6-fluorochroman-4-amine, 7-fluorochroman-4-amine, 5,8-difluorochroman-4-amine, and 6,8-difluorochroman-4-amine were resolved via the procedure described above for the resolution of 8-fluorochroman-4-amine.

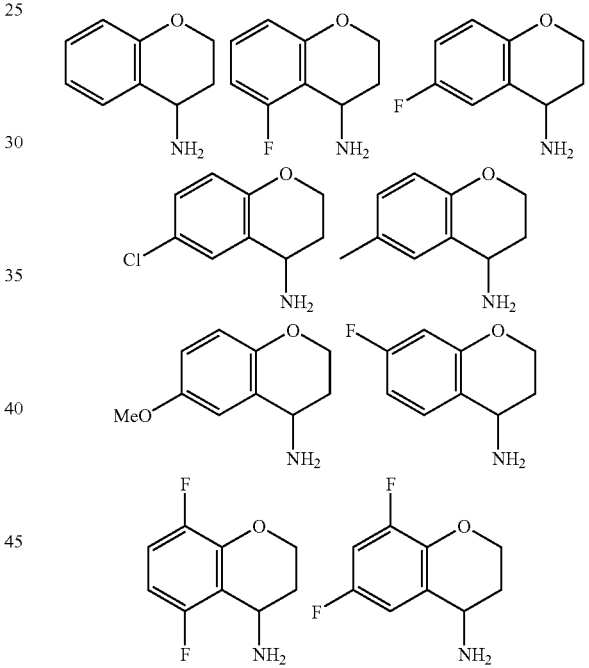

Synthesis of 8-substituted 2-(imidazolo[4,5-c]pyridinyl)purines

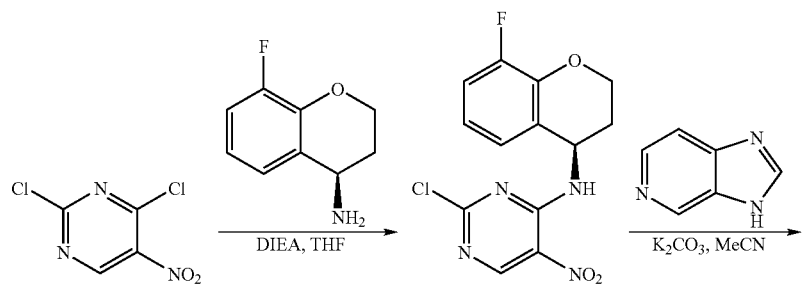

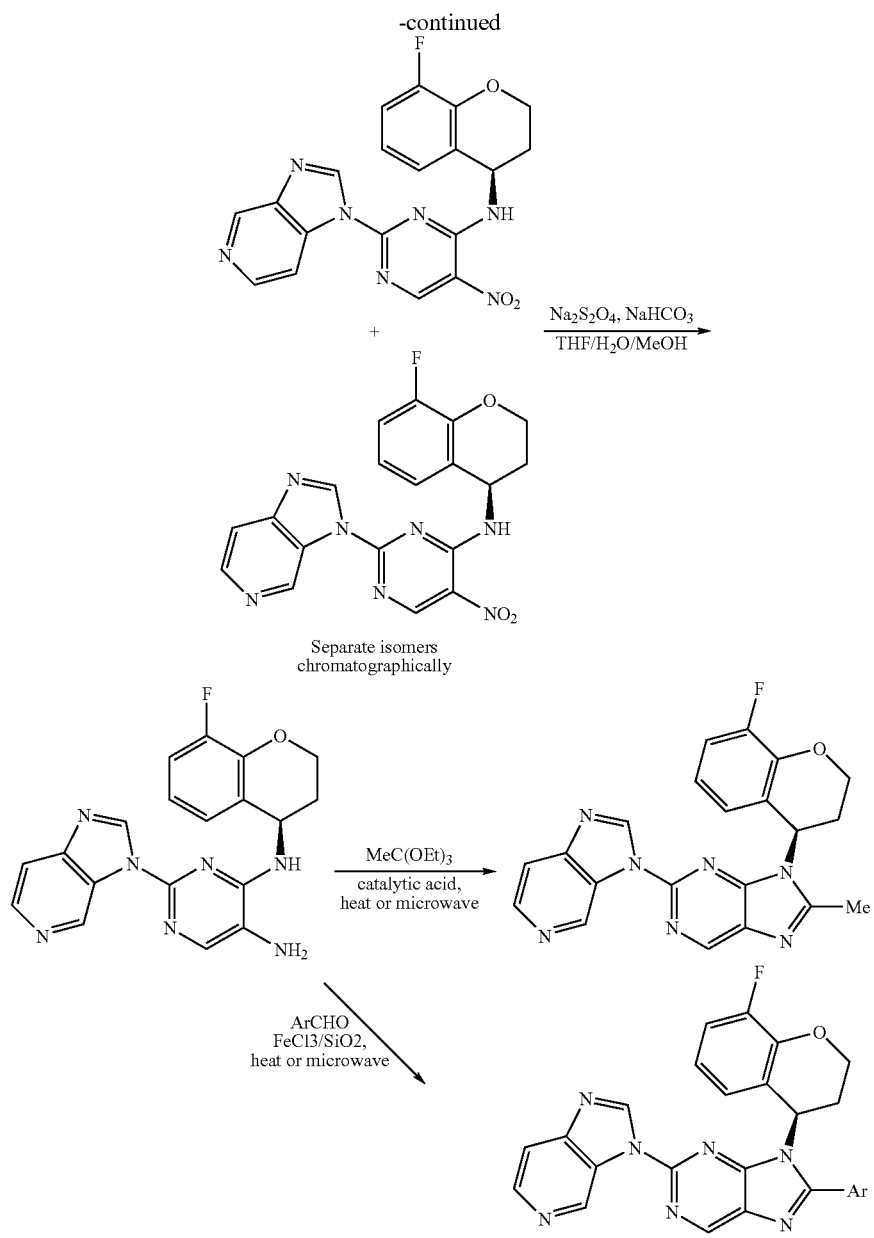

(R)-2-Chloro-N-(8-fluorochroman-4-yl)-5-nitropyrimidin-4-amine: (R)-8-fluorochroman-4-amine (60 mg) was added to a solution of 2,4-dichloro-5-nitropyrimidine (70 mg) and DIEA (0.14 mL) in THF (5 mL) at −78° C. The reaction mixture was stirred for a further 15 min at −78° C. then removed from the cold bath and allowed to warm to RT. A one molar solution of the sodium salt of benzimidazole (0.7 ml, stock solution prepared via the addition of sodium hydride to a benzimidazole solution in THF) was added to the reaction intermediate ((R)-2-chloro-N-(8-fluorochroman-4-yl)-5-nitropyrimidin-4-amine) and the resulting mixture was stirred at RT overnight. Purification via column chromatography (elution with 1 MeOH/DCM) gave the titled compound (120 mg), $MH^+=407$.

N—((R)-8-Fluorochroman-4-yl)-2-(3H-imidazo[4,5-c]pyridin-3-yl)-5-nitropyrimidin-4-amine. A solution of (R)-2-chloro-N-(8-fluorochroman-4-yl)-5-nitropyrimidin-4-amine in acetonitrile was treated with 3H-imidazo[4,5-c]pyridine and potassium carbonate. The mixture was stirred at reflux for 6 hours, cooled to room temperature, diluted with 150 mL of EtOAc, and washed twice with 30 mL portions of water. The organic layer was separated, dried with magnesium sulfate, filtered, and concentrated in vacuo. Purification by column chromatography (1% MeOH/DCM) provided N—((R)-8-fluorochroman-4-yl)-2-(3H-imidazo[4,5-c]pyridin-3-yl)-5-nitropyrimidin-4-amine as the first eluting isomer: ($^1$H-NMR (300 MHz, CDCl$_3$) δ 9.8 (s, 1H), 9.4 (s, 1H), 9.2 (s, 1H), 8.9 (d, 1H), 8.6 (d, 1H), 7.8 (d, 1H), 7.1 (m, 2H), 6.9 (m, 1H), 5.8 (q, 1H), 4.6 (m, 1H), 4.4 (m, 1H), 2.6 (m, 1H), 2.4 (m, 1H).). N—((R)-8-Fluorochroman-4-yl)-2-(1H-imidazo[4,5-c]pyridin-1-yl)-5-nitropyrimidin-4-amine eluted second: (1H-NMR (300 MHz, CDCl$_3$) δ 9.4 (s, 1H), 9.2 (s, 1H), 9.1 (s, 1H), 8.9 (d, 1H), 8.6 (d, 1H), 8.4 (d, 1H), 7.1 (m, 2H), 6.9 (m, 1H), 5.7 (q, 1H), 4.5 (m, 1H), 4.4 (m, 1H), 2.6 (m, 1H), 2.4 (m, 1H).).

$N^4$—((R)-8-Fluorochroman-4-yl)-2-(3H-imidazo[4,5-c]pyridin-3-yl) pyrimidine-4,5-diamine. To a solution of N—((R)-8-Fluorochroman-4-yl)-2-(3H-imidazo[4,5-c]pyridin-3-yl)-5-nitropyrimidin-4-amine in THF was added a solution of sodium hydrosulfite and sodium bicarbonate in water. The mixture briefly became blue followed by colorless. Methanol was added to maintain the homogeneity of the solution. The mixture was diluted with EtOAc and washed twice with brine. The aqueous washes were extracted with another portion of EtOAc and then the combined organic layers were dried over sodium sulfate and concentrated in vacuo to provide the title diamine which was taken to the next step without further purification.

9-((R)-8-Fluorochroman-4-yl)-2-(3H-imidazo[4,5-c]pyridin-3-yl)-8-methyl-9H-purine. To a microwave vial is added the above diamine, a catalytic amount of an acid such as para-toluene sulfonic acid monohydrate and excess triethyl orthoacetate (2-1000 fold) in a suitable polar solvent such as ethanol, butanol, dioxane and the like (or mixtures thereof). The vial is capped and the solution is heated in an Emrys Optimizer microwave at 100-180° C. for 1-4 hr. Alternatively the condensation is affected by reflux in the appropriate solvent or heating in a sealed tube. The reaction mixture is evaporated in vacuo. A basic work up followed by chromatography (silica gel/DCM-MeOH) provides the title compound. Other 8-alkyl purines are similarly made by using appropriate ortho esters. 8-Arylpurines are prepared by condensation of the diamine with the appropriate aromatic or heteroaromatic carboxaldehyde with catalytic iron trichloride/silica gel (see Example O).

Synthesis of 8-fluoro-3,4-dihydro-1H-isochromen-4-amine

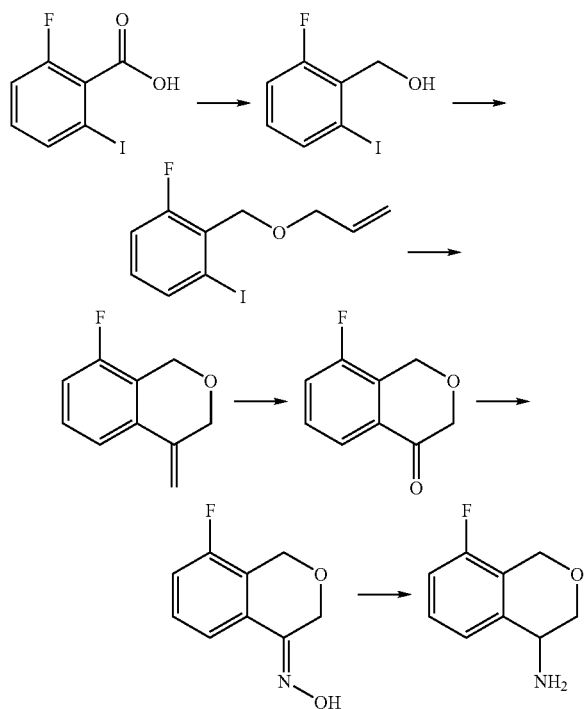

(2-Fluoro-6-iodophenyl)methanol. To a stirred solution of 2-fluoro-6-iodobenzoic acid (10 mmol) in THF (6.5 mL) and trimethylborate (3.25 mL) was added borane dimethylsulfide (12 mmol) slowly, maintaining the internal temperature at 20-25° C. Stirring was continued for an additional 16 h at room temperature and then methanol (1.44 mL) was added cautiously. The resulted solution was evaporated in vacuo to offer 2.5 g of the title compound as a pale yellow oil.

2-(Allyloxymethyl)-1-fluoro-3-iodobenzene. To a solution of (2-fluoro-6-iodophenyl)methanol (10 mmol) in 50 mL of THF was added NaH (12 mmol) in small portions at room temperature. After the addition, allylbromide (12 mmol) was added slowly via syringe. The reaction mixture was stirred 16 hours at room temperature. The resulting white heterogeneous mixture was quenched with water and then diluted with 100 mL of Et$_2$O, followed by washing with water and brine. The organic layer was dried over MgSO$_4$ and then concentrated to dryness in vacuo to offer 2.8 g of the title compound.

8-Fluoro-4-methylene-3,4-dihydro-1H-isochromene. 2-(Allyloxymethyl)-1-fluoro-3-iodobenzene (1 g) was dissolved in 20 mL of CH$_3$CN and 2.4 mL of Et$_3$N. The reaction solution was vacuum degassed three times, followed by the addition of Pd(OAc)$_2$ (37.6 mg) and PPh$_3$ (89.8 mg). The resulting mixture was heated at 80° C. for 16 hours. The reaction mixture was cooled to room temperature and diluted with Et$_2$O. The organic layer was washed with 1N HCl, 10% aqueous NaHCO$_3$, brine, and then dried over Na$_2$SO$_4$. After filtration, the filtrate was concentrated to dryness to offer a brown oil, which was purified by flash chromatography to offer 200 mg of the title compound.

8-Fluoro-1H-isochromen-4(3H)-one. 8-Fluoro-4-methylene-3,4-dihydro-1H-isochromene (400 mg) was dissolved in a solution of 1:1 MeOH/DCM (50 mL) and 1 mL of pyridine added. The mixture was chilled to −78° C. and ozone was bubbled through the mixture for 40 min. The reaction monitored by TLC. The mixture was purged with nitrogen at −78° C. for 10 min and then treated with PPh$_3$. After concentration, the resulting residue was purified by preparative TLC to offer 300 mg of the title compound.

8-Fluoro-3,4-dihydro-1H-isochromen-4-amine. The title compound was prepared from 8-fluoro-1H-isochromen-4 (3H)-one via the procedure described above for the synthesis of 8-fluorochroman-4-amine.
$^1$H-NMR (300 MHz, CD$_3$OD) δ 7.4 (m, 1H), 7.3 (d, 1H), 7.2 (m, 1H), 5.0 (d, 1H), 4.7 (d, 1H), 4.4 (s, 1H), 4.2 (d, 1H) 3.9 (d, 1H) ppm.

Synthesis of trans-4-methoxycyclohexanamine

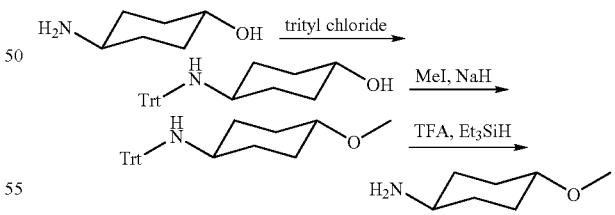

Trans-4-(tritylamino)cyclohexanol. Trans-4-aminocyclohexanol (2.6 g, 22.6 mmol) was suspended in 60 mL DCM, then 4 mL (28.7 mmol) triethylamine was added. The mixture was cooled in ice bath, and trityl chloride (6.3 g, 22.6 mmol) was added. The mixture was stirred overnight, allowing it to slowly warm up. Saturated NaHCO$_3$ was added to quench the chloride, and product was extracted with EtOAc three times. The combined organic layer was washed with brine, and dried over Na$_2$SO$_4$. Column chromatography with 20-40% EtOAc in hexanes provided 5.3 g (66%) white solid.

Trans-4-methoxy-N-tritylcyclohexanamine. Above solid (2.6 g, 7.3 mmol) was dissolved in 30 mL anhydrous THF, cooled in ice bath, then added 0.60 g (15 mmol) sodium hydride (60% dispersion in mineral oil). Iodomethane (0.46 mL, 7.3 mmol) was added, and the resulting white suspension was allowed to slowly warm to room temperature and stirred overnight under an empty balloon. TLC showed the completion of reaction. The mixture was quenched carefully with sat. NH₄Cl, and extracted with EtOAc three times. Column chromatography with 10-20% EtOAc in hexanes provided 2.37 g (88%) white solid as the desired product.

Trans-4-methoxycyclohexanamine. The above solid was dissolved in 30 mL 30% TFA in DCM, and 1 mL Et₃SiH was added. The solvents were removed after 15 minutes, and the residue was dried under high vacuum for 2 hours to give yellow solid. This solid was dissolved in 1:3 EtOAc: 0.25M aq. HCl. The organic layer was removed, and the aq. layer was washed with EtOAc two more times. Remove water under high vacuum gave 0.98 g (~95% yield) white solid as the HCl salt of the desired amine.

$^1$H NMR (300 MHz, CDCl$_3$): δ 8.3 (bs, 2H), 3.3 (s, 3H), 3.1-3.2 (m, 2H), 2.1-2.3 (m, 4H), 1.5-1.7 (br q, 2H), 1.2-1.4 (br q, 2H) ppm.

Synthesis of (1R,4R)-4-(tert-butyldiphenylsilyloxy)-1,2,3,4-tetrahydronaphthalen-1-amine

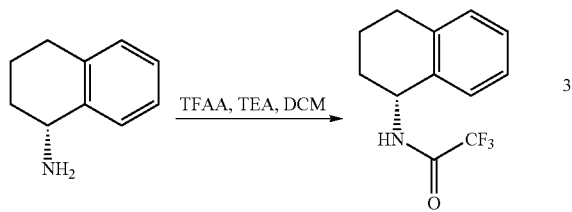

(R)-2,2,2-trifluoro-N-(1,2,3,4-tetrahydronaphthalen-1-yl)acetamide. A 250 ml round bottom flask was charged with 5 g (34 mmol) of (R)-1,2,3,4-tetrahydronaphthalen-1-amine (Alfa Aesar). The flask was then purged with argon. 50 ml of DCM was then added, and the solution was cooled to 0° C. 9.48 ml (68 mmol) of TEA was added by syringe, then 7.09 ml (51 mmol) of trifluoroacetic anhydride was added slowly by syringe. The solution was then stirred overnight, slowly warming to room temp. The mixture was diluted with DCM and washed with water, 1 N HCl, and brine. The organic layer was dried over MgSO₄ and concentrated in vacuo, and purified by column chromatography (eluting with 1:1 DCM: Hex), to give 6.63 g (80%) of the titled compound.

$^1$H-NMR (CDCl$_3$) δ 7.2 (m, 3H), 7.1 (t, 1H), 6.5 (br s, 1H), 5.2 (q, 1H), 2.8 (q, 2H), 2.1 (m 1H), 1.9 (m, 3H) ppm.

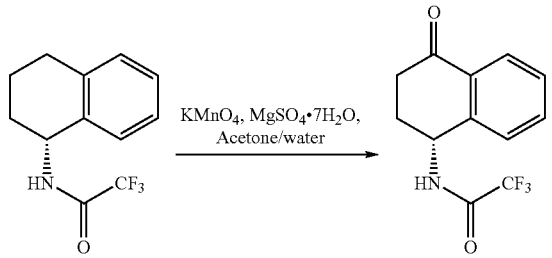

(R)-2,2,2-trifluoro-N-(4-oxo-1,2,3,4-tetrahydronaphthalen-1-yl)acetamide. To a cooled solution of 1 g (4.1 mmol) of (R)-2,2,2-trifluoro-N-(1,2,3,4-tetrahydronaphthalen-1-yl)acetamide in acetone (30 mL) at 0° C., was added a solution of 2.03 g (8.2 mmol) MgSO₄.7H₂O in 15 mL of water. After 5 min of stirring, 1.95 g (12.3 mmol) of KMnO₄ was added in small portions over 1 hr. The mixture was then stirred overnight, slowly warming to room temp. The mixture was filtered. The filtrate was treated with saturated sodium metabisulfite and filtered. The filtrate was extracted with DCM several times. The combined organic extracts were washed with distilled water and brine, dried over MgSO₄ and concentrated in vacuo to afford 0.96 g (91%) of the title compound, whose purity was good enough to use crude.

$^1$H-NMR (CDCl$_3$) δ 8.2 (d, 1H), 7.7 (t, 1H), 7.6 (t, 1H), 7.5 (d, 1H), 6.8 (br s, 1H), 5.5 (m, 1H), 2.9 (m, 2H), 2.6 (m 1H), 2.4 (m, 1H) ppm.

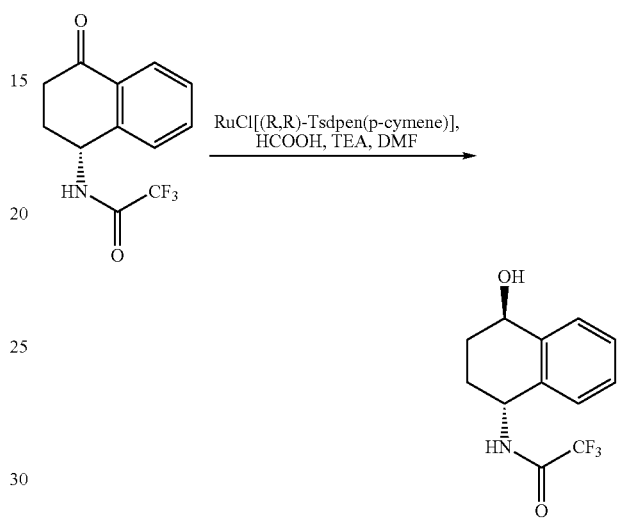

2,2,2-Trifluoro-N-((1R,4R)-4-hydroxy-1,2,3,4-tetrahydronaphthalen-1-yl)acetamide. Purge a 100 ml round bottom flask containing 0.50 g (1.95 mmol) of (R)-2,2,2-trifluoro-N-(4-oxo-1,2,3,4-tetrahydronaphthalen-1-yl)acetamide and 0.062 g (0.098 mmol) RuCl[(R,R)-Tsdpen(p-cymene)] with argon (catalyst prepared using procedure from Org Syn, Vol 82, pg 10-17, note 5). Add 25 ml of dry DMF by syringe and stir. To this solution was added a mixture of 0.43 ml (3.11 mmol) of triethylamine and 0.12 ml (3.11 mmol) of HCOOH. The reaction mixture was stirred at 50° C. overnight. To complete the reaction, additional RuCl[(R,R)-Tsdpen(p-cymene)] (0.062 g), triethylamine (0.43 ml) and HCOOH (0.12 ml) were added and stirring continued at 50° C. for an additional 6-8 hr. The reaction mixture was cooled to room temp, then diluted with 150 ml EtOAc, and washed with 20 ml distilled water. The organic phase was dried over MgSO₄ and concentrated in vacuo, and purified by column chromatography (eluting with 1% MeOH in DCM), to give 0.417 g (83%) of the titled compound.

$^1$H-NMR (CDCl$_3$) δ 7.5 (d, 1H), 7.3 (m, 2H), 7.2 (d, 1H), 6.4 (br s, 1H), 5.3 (q, 1H), 4.8 (d, 1H), 2.4 (m, 1H), 2.2 (m 1H), 1.8 (m, 2H) ppm.

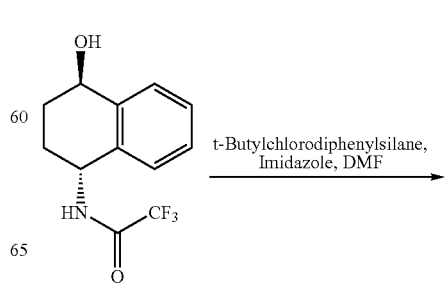

-continued

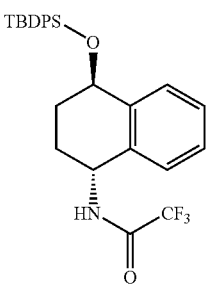

N-((1R,4R)-4-(tert-butyldiphenylsilyloxy)-1,2,3,4-tetrahydronaphthalen-1-yl)-2,2,2-trifluoroacetamide. To a 250 ml round bottom flask containing 2.2 g (8.49 mmol) of 2,2,2-trifluoro-N-((1R,4R)-4-hydroxy-1,2,3,4-tetrahydronaphthalen-1-yl)acetamide and 1.73 g (25.48 mmol) of imidazole was added 35 ml of DMF, and stirring was started. To this solution was added 4.67 g (16.99 mmol) of t-butylchlorodiphenylsilane. The reaction mixture was stirred at room temperature overnight. The reaction mixture was diluted with 150 ml EtOAc, and washed with 20 ml distilled water. The organic phase was dried over $MgSO_4$ and concentrated in vacuo and purified by column chromatography (eluting with 1:1 DCM:Hex), to give 4.0 g (95%) of the titled compound.

$^1$H-NMR (CDCl$_3$) δ 7.7 (d, 2H), 7.6 (d, 2H), 7.4 (m, 6H), 7.2 (m, 4H), 6.3 (br s, 1H), 5.2 (q, 1H), 4.8 (t, 1H), 2.4 (m, 1H), 1.8 (m, 2H), 1.6 (m, 1H) ppm.

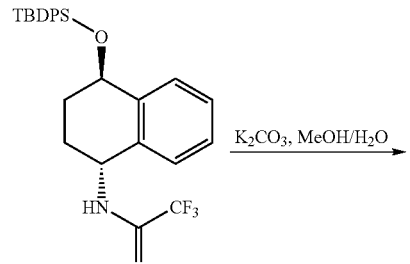

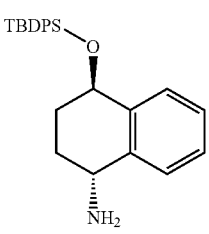

(1R,4R)-4-(tert-Butyldiphenylsilyloxy)-1,2,3,4-tetrahydronaphthalen-1-amine. To a 250 ml round bottom flask containing 4 g (8.0 mmol) of N-((1R,4R)-4-(tert-butyldiphenylsilyloxy)-1,2,3,4-tetrahydronaphthalen-1-yl)-2,2,2-trifluoroacetamide was added 160 ml of MeOH. To this solution was added a solution of 8.34 g (60 mmol) potassium carbonate in 16 ml of water. The reaction mixture was stirred at room temp overnight. The reaction mixture was diluted with 150 ml EtOAc, and after separation, the aqueous phase was extracted several times with EtOAc. The organic phase was dried over $MgSO_4$ and concentrated in vacuo to afford 3.09 g (96%) of the title compound, whose purity was good enough to use crude. (Note: On separate occasion, this hydrolysis became sluggish, and 30 ml of 3M NaOH was added, upon which the reaction was completed in a few hours.)

$^1$H-NMR (CDCl$_3$) δ 7.7 (d, 2H), 7.6 (d, 2H), 7.4 (m, 7H), 7.2 (m, 3H), 4.8 (t, 1H), 4.2 (t, 1H), 3.8 (br s, 2H), 2.4 (m, 1H), 1.8 (m, 2H), 1.6 (m, 1H) ppm.

Synthesis of 4-(2,4-dimethoxybenzylamino)-3-(5-nitro-4-thiocyanatopyrimidin-2-ylamino)benzonitrile

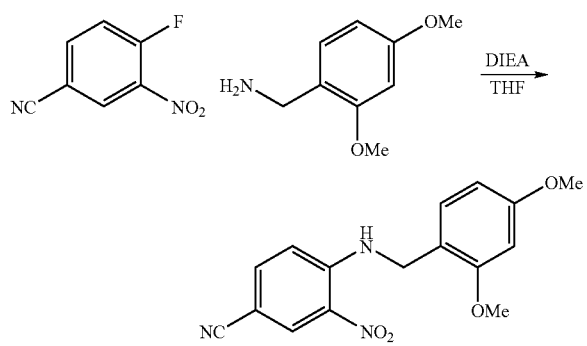

4-(2,4-Dimethoxybenzylamino)-3-nitrobenzonitrile. A solution of 4-fluoro-3-nitrobenzonitrile (5.0 g) in THF (100 mL) was treated with DIEA (6.3 mL) and 2,4-dimethoxybenzylamine (5.0 mL), and then stirred for 24 h. The solvent was evaporated and the crude mixture was dissolved in EtOAc (100 mL). The solution was washed once with 1 M HCl and twice with saturated aqueous NaCl (100 mL each). The organic layer was separated, dried over $Na_2SO_4$, filtered, and concentrated in vacuo. Column chromatography (20% EtOAc in DCM) provided 9.25 g of the title compound.

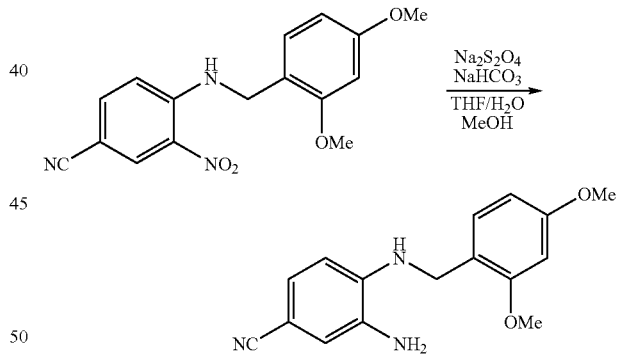

4-(2,4-Dimethoxybenzylamino)-3-aminobenzonitrile. A solution of 4-(2,4-dimethoxybenzylamino)-3-nitrobenzonitrile (4.54 g) in THF (400 mL) was treated with a solution of sodium hydrosulfite (20 g) and sodium bicarbonate (10 g) in distilled water (350 mL). Enough methanol was immediately added (50 mL) to maintain a homogeneous solution. After 15 minutes, EtOAc (500 mL) and saturated aqueous NaCl (500 mL) were added and the organic layer was separated. The aqueous layer was extracted again with 400 mL EtOAc. The combined organic layers were washed with saturated aqueous NaCl (500 mL) and separated. The organic phase was dried over $Na_2SO_4$, filtered, and concentrated in vacuo to provide 4.33 g of the title compound.

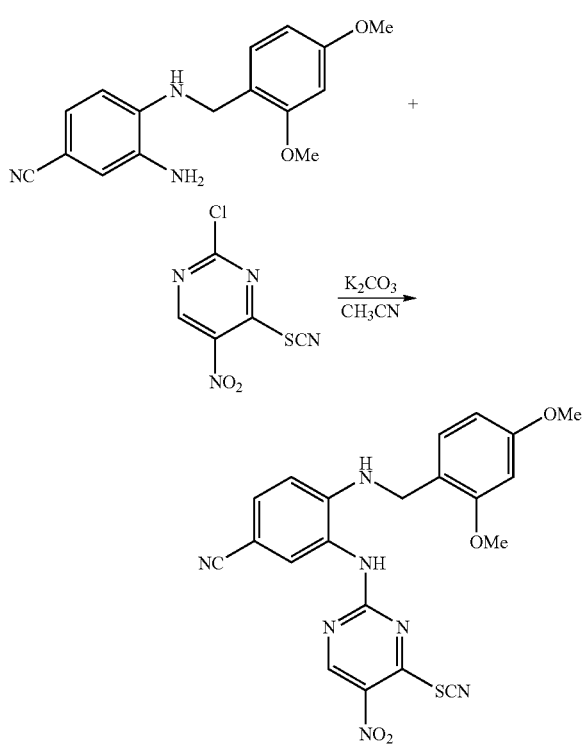

4-(2,4-Dimethoxybenzylamino)-3-(5-nitro-4-thiocyanatopyrimidin-2-ylamino)benzonitrile. A solution of 4-(2,4-dimethoxybenzylamino)-3-aminobenzonitrile (3.9 g) in acetonitrile (100 mL) was cooled to 0° C. and treated with potassium carbonate (6.3 g) followed by a solution containing 3 g of 2-chloro-5-nitro-4-thiocyanatopyrimidine (WO 2003/032994) in acetonitrile (50 mL). The mixture was stirred for 30 minutes at 0° C. and 30 minutes at room temperature resulting in the formation of a precipitate. The mixture was quenched at 0° C. by the addition of 4% acetic acid (150 mL) and filtered. The precipitate was swirled in 100 mL acetonitrile and filtered again. The precipitate was washed with acetonitrile, which resulted in the slow dissolution of product into the filtrate. After air-drying, 1.5 g of the title compound remained as the precipitate cake. The filtrate was extracted with EtOAc, dried over Na$_2$SO$_4$, filtered, and concentrated in vacuo. Column chromatography (0→20% EtOAc/DCM) and recrystallization from acetonitrile provided 0.415 g of additional title compound.

Synthesis of tert-butyl 4-fluoro-2-(5-nitro-4-thiocyanatopyrimidin-2-ylamino)phenylcarbamate

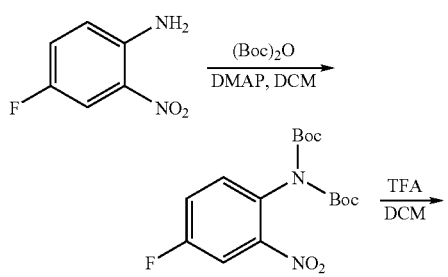

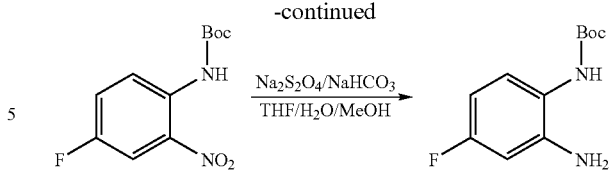

4-Fluoro-2-nitro-phenyl di-tert-butyl imidodicarbonate. A catalytic amount of DMAP was added to a mixture of 4-fluoro-2-nitrobenzenamine (0.78 g) and di-tert-butyl dicarbonate (2.18 g) in DCM (20 mL) and stirred at room temperature for 15 hr. The mixture was diluted with H$_2$O and twice extracted with DCM, the combined organics were dried, filtered and evaporated to yield the bis-BOC material (quant).
$^1$H-NMR (300 MHz, CDCl$_3$) δ 7.8 (dd, 1H), 7.3 (m, 2H), 1.4 (s, 18H) ppm.

tert-Butyl 4-fluoro-2-nitrophenylcarbamate. (procedure: Connell, R. D.; Rein, T.; Akermark, B.; Helquist, P. J. *J. Org. Chem.* 1988, 53, 3845) To a stirred solution of the Bis-BOC material in DCM (20 mL) was added TFA (0.58 mL). After 3 hr the reaction was quenched with aq. NaHCO$_3$ (5 mL), brine was added, the mixture separated and extracted with additional DCM. The combined organics were evaporated, purified via column chromatography (eluted with 7.5% EtOAc/Hex) to give 1.12 g titled product.
$^1$H-NMR (300 MHz, CDCl$_3$) δ 9.5 (br 1H), 8.5 (dd, 1H), 7.9 (dd, 1H), 7.3 (m, 1H), 1.5 (s, 9H) ppm.

tert-Butyl 2-amino-4-fluorophenylcarbamate. To a solution of tert-butyl 4-fluoro-2-nitrophenylcarbamate (0.34 g) in THF (30 mL) was added a premixed solution of sodium hydrosulfite (2 g) and sodium bicarbonate (1 g) in water (50 mL). MeOH (10 mL) was also added to aid solution of the mixture, which was stirred at room temperature for 30 min, when sodium chloride was added to saturate the solution. The resulting mixture was extracted with EtOAc (2×). The combined organics were dried, filtered and evaporated to yield the titled compound (quant) that was used as such for the next step. $^1$H-NMR (300 MHz, CDCl$_3$) δ 7.5 (dd, 1H), 6.6 (dd, 1H), 6.5 (m, 1H), 6.4 (br 1H), 4.7 (br 2H), 1.5 (s, 9H) ppm; MH$^+$=227 (minor), 127 (-BOC), 171 (-tBu).

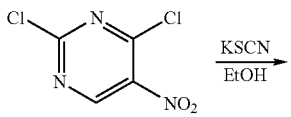

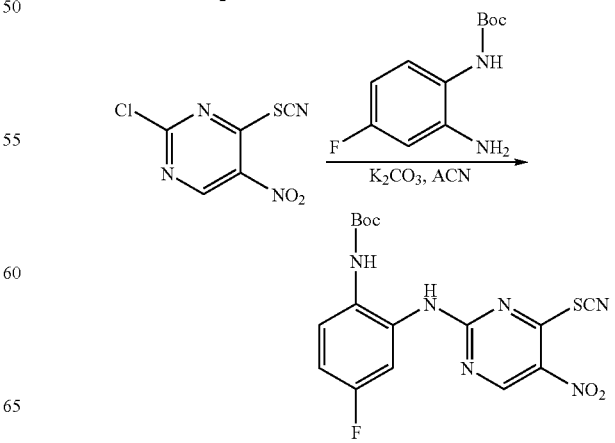

2-Chloro-5-nitro-4-thiocyanatopyrimidine. (compound known, e.g. WO 2003/032994) Potassium thiocyanate (0.97 g, 10 mM) was added to a solution of 2,4-dichloro-5-nitropyrimidine (1.94 g 10, mM) in EtOH (40 mL) cooled to 0° C. via an ice bath. The solution was stirred at 0° C. for 30 min, then the bath was removed and the resulting suspension allowed to come to RT over 60 min, when water (100 mL) was added. The precipitate was collected via filtration, washed with ice cold water, dissolved with DCM, dried (MgSO$_4$), filtered and evaporated to yield the titled compound (1.7 g).

$^1$H NMR (300 MHz, CDCl$_3$) δ 9.4 (s, 1H) ppm.

tert-Butyl 4-fluoro-2-(5-nitro-4-thiocyanatopyrimidin-2-ylamino)phenylcarbamate. Potassium carbonate (207 mg) was added to a stirred solution of 2-chloro-5-nitro-4-thiocyanatopyrimidine (108 mg) and tert-butyl 4-fluoro-2-nitrophenylcarbamate (113 mg) in ACN (5 mL) and stirred for 15 hr. The solution was diluted with brine and extracted with EtOAc (2×). The combined organics were evaporated and purified via column chromatography, elution with 30% EtOAc/Hex gave the titled compound (144 mg, 71% yield).

$^1$H-NMR (300 MHz, DMSO-d6) δ 10.5 (br s, 1H), 9.3 (br s, 1H), 8.9 (br s, 1H), 7.7-7.4 (m, 2H), 7.1 (br s, 1H), 1.5 (s, 9H), 1.5 (s, 9H) ppm; MH$^+$=407, 307 (-BOC), 351 (-tBu).

Some similar thiocyanatopyrimidines, such as tert-butyl 4-chloro-2-(5-nitro-4-thiocyanatopyrimidin-2-ylamino)phenylcarbamate, tert-butyl 2-(5-nitro-4-thiocyanatopyrimidin-2-ylamino)-4-(trifluoromethyl)phenylcarbamate, and tert-butyl 2-(5-nitro-4-thiocyanatopyrimidin-2-ylamino)-4-(trifluoromethoxy)phenylcarbamate, were prepared via procedures described above for the synthesis of tert-butyl 4-fluoro-2-(5-nitro-4-thiocyanatopyrimidin-2-ylamino)phenylcarbamate, from corresponding 4-chloro-2-nitrobenzenamine, 2-nitro-4-(trifluoromethyl)benzenamine and 2-nitro-4-(trifluoromethoxy)benzenamine.

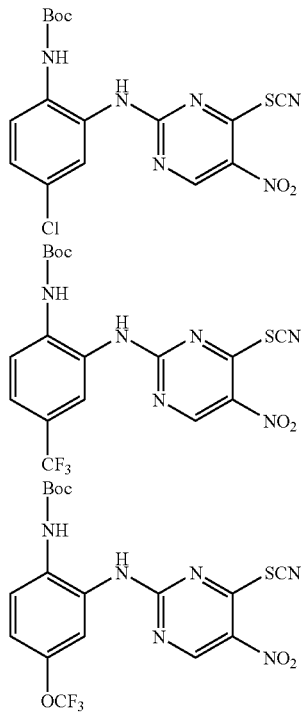

Synthesis of 3-(5-nitro-4-thiocyanatopyrimidin-2-yl)-3H-benzo[d]imidazole-5-carbonitrile

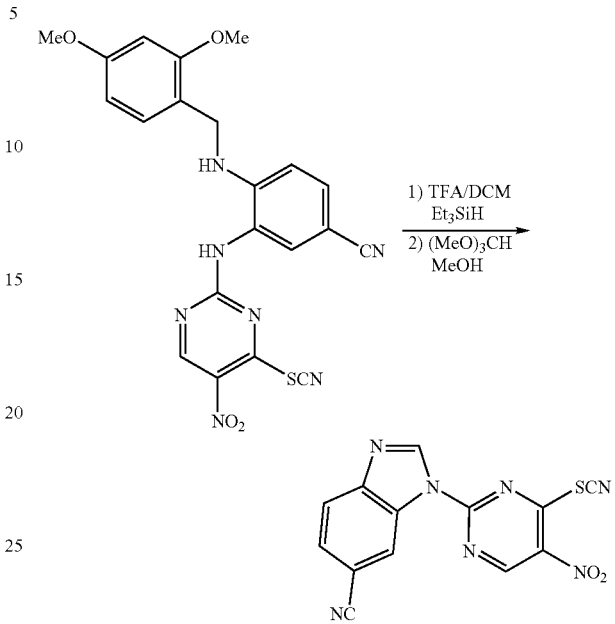

To the solution of 0.58 g (1.25 mmol) 4-(2,4-dimethoxybenzylamino)-3-(5-nitro-4-thiocyanatopyrimidin-2-ylamino)benzonitrile in 10 mL 30% (v/v) TFA in DCM was added 0.01 mL of triethylsilane. The mixture was stirred for 0.5 hr. LCMS indicated the completion of de-protection. A red residue was obtained after removing the volatiles on rotary evaporator, and was suspended (majority dissolved) in 10 mL 1:1 trimethyl orthoformate: MeOH. The resulting mixture was stirred for 2 hrs at room temperature. Yellow solids were precipitated. Desired product (0.38 g, 95% overall yield) was obtained after suction filtration and washing with cold MeOH twice.

MS (ESI), m/z 324 ([M+H]$^+$).

$^1$H-NMR (300 MHz, CDCl$_3$+10% CD$_3$OD) δ 9.5 (s, 1H), 9.2 (s, 1H), 9.1 (s, 1H), 7.9 (d, 1H), 7.7 (d, 1H) ppm.

Synthesis of 6-fluoro-1-(5-nitro-4-thiocyanatopyrimidin-2-yl)-1H-benzo[d]imidazole

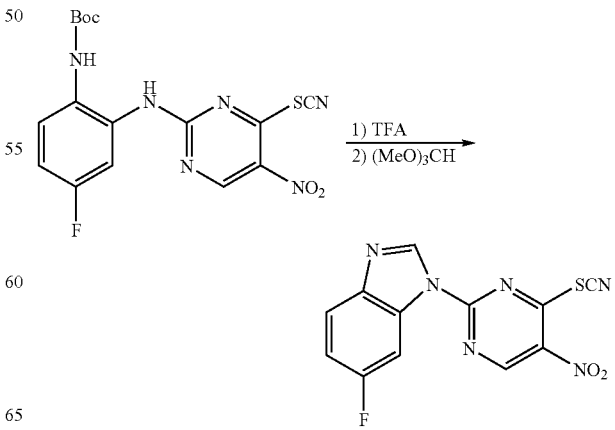

tert-Butyl 4-fluoro-2-(5-nitro-4-thiocyanatopyrimidin-2-ylamino)phenylcarbamate (4.06 g) was dissolved in 30% TFA in DCM (50 mL) and stirred until no starting material remained (90 min). The reaction solvents were removed, to yield crude 5-fluoro-N'-(5-nitro-4-thiocyanatopyrimidin-2-yl)benzene-1,2-diamine (MH$^+$=306) as a TFA salt that was used immediately as such in the next step.

Trimethyl ortho formate (15 mL) and MeOH (100 mL) were added to the above diamine and the solution was stirred for 16 hrs. The resulting orange ppt was collected via filtration, washed with MeOH and dried under reduced pressure to yield the titled compound (2.62 g).

MS (ESI), m/z 317 ([M+H]$^+$).

$^1$H NMR (DMSO-d$_6$) δ 9.2 (s, 1H), 9.1 (s, 1H), 8.5 (dd, 1H), 7.8 (dd, 1H), 7.3 (dd, 1H) ppm.

Some similar (5-nitro-4-thiocyanatopyrimidin-2-yl)-1H-benzo[d]imidazoles, such as 6-chloro-1-(5-nitro-4-thiocyanatopyrimidin-2-yl)-1H-benzo[d]imidazole, 1-(5-nitro-4-thiocyanatopyrimidin-2-yl)-6-(trifluoromethyl)-1H-benzo[d]imidazole and 1-(5-nitro-4-thiocyanatopyrimidin-2-yl)-6-(trifluoromethoxy)-1H-benzo[d]imidazole were prepared via procedure described above for the synthesis of 6-fluoro-1-(5-nitro-4-thiocyanatopyrimidin-2-yl)-1H-benzo[d]imidazole, from corresponding tert-butyl 4-chloro-2-(5-nitro-4-thiocyanatopyrimidin-2-ylamino)phenylcarbamate, tert-butyl 2-(5-nitro-4-thiocyanatopyrimidin-2-ylamino)-4-(trifluoromethyl)phenylcarbamate, and tert-butyl 2-(5-nitro-4-thiocyanatopyrimidin-2-ylamino)-4-(trifluoromethoxy)phenylcarbamate.

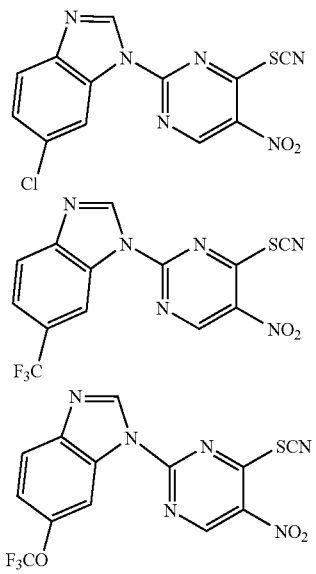

Synthesis of 2-aminopyrimidine-4-carboxaldehyde
(*Bioorg. Med. Chem. Lett.,* 1998, 8, 3111)

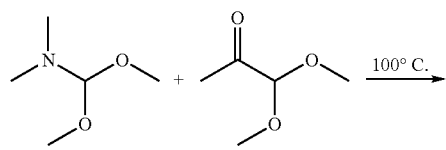

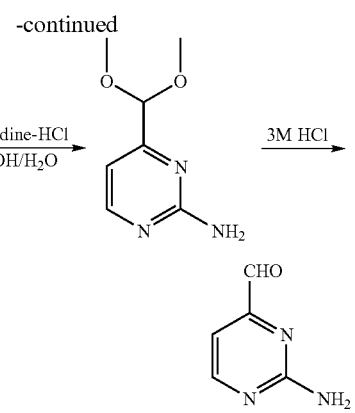

2-Aminopyrimidine-4-carboxaldehyde dimethylacetal. A solution of 5.5 ml (41 mmol, 1 eq.) of dimethylformamide dimethyl acetal and 5.0 ml (41 mmol, 1 eq.) pyrvuric aldehyde dimethyl acetal was heated at 100° C. for 16 h. Methanol was removed in vacuo to afford an oil. A solution of NaOH (1.8 g, 45 mmol, 1.1 eq.) in 5 mL of H$_2$O was added to a solution of 4.3 g (45 mmol, 1.1 eq.) of guanidine HCl in 10 mL of H$_2$O. The resulting solution was added to the above described oil. The resulting mixture was stirred at r.t. for 48 h. Filtration afforded 2.5 g (50%) of 2-aminopyrimidine-4-carboxaldehyde dimethylacetal.

2-Aminopyrimidine-4-carboxaldehyde. A solution of 2.5 g (15 mmol, 1.0 eq.) 2-aminopyrimidine-4-carboxaldehyde dimethylacetal in 16 ml (45 mmol, 3 eq.) of 3M HCl was heated at 48° C. for 14 h. The mixture was cooled to r.t. and layered with 50 mL of EtOAc. The aqueous layer was neutralized with NaHCO$_3$ and then extracted with EtOAc (5×50 ml). The combined extracts were dried (Na$_2$SO$_4$) and concentrated in vacuo afford 0.69 g (37%) of 2-aminopyrimidine-4-carboxaldehyde.

$^1$H NMR (300 MHz, CDCl$_3$): δ 9.82 (s, 1H), 8.75 (d, 1H), 7.10 (d, 1H), 5.28 (s, 2H) ppm.

Example A

Synthesis of 3-(9-((R)-8-fluorochroman-4-yl)-8-(pyrimidin-5-yl)-9H-purin-2-yl)-3H-benzo[d]imidazole-5-carbonitrile

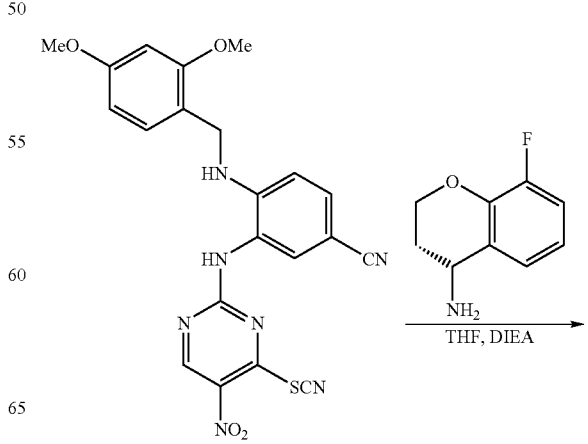

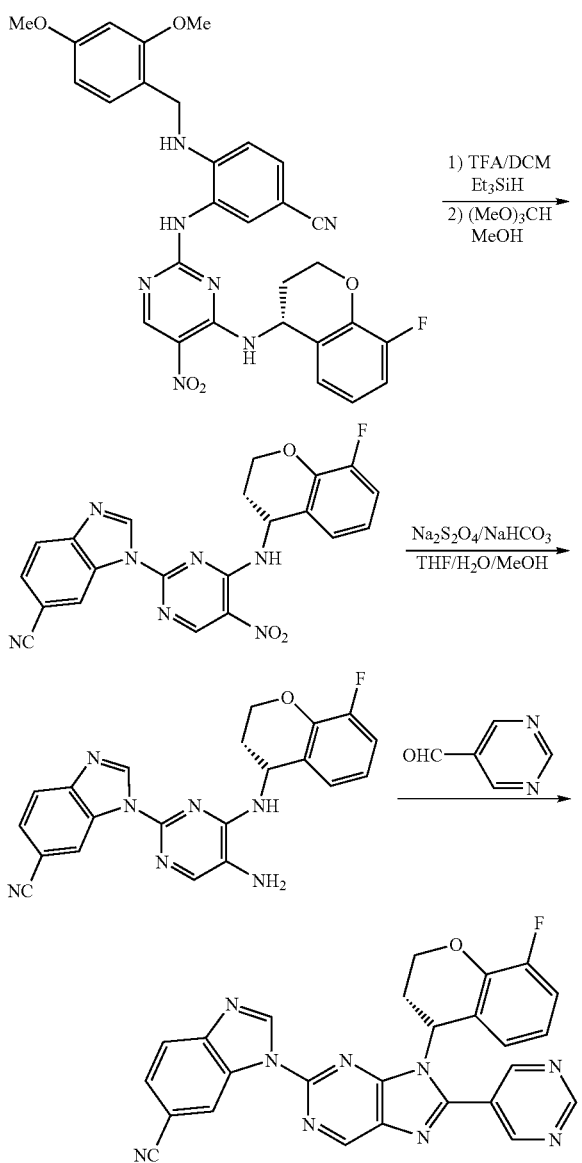

Example 13

(R)-4-(2,4-Dimethoxybenzylamino)-3-(4-(8-fluorochroman-4-ylamino)-5-nitropyrimidin-2-ylamino)benzonitrile. (R)-8-Fluorochroman-4-amine (HCl salt, 0.45 g, 2.2 mmol) was dissolved in 1 mL DMSO with 1.7 mL N,N-diisopropylethyl amine (9.7 mmol) in 40 mL anhydrous THF. To this solution was added 0.93 g (2.0 mmol) 4-(2,4-dimethoxybenzylamino)-3-(5-nitro-4-thiocyanatopyrimidin-2-ylamino)benzonitrile. The slightly cloudy mixture was stirred at room temperature for 16 hrs under Argon balloon till HPLC showed the completion of reaction. The mixture became clear then. The reaction mixture was diluted with EtOAc, washed with brine twice, and then dried over Na₂SO₄. Solvents were removed under vacuum to give 1.1 g dark red solid as the crude product.

3-(4-((R)-8-Fluorochroman-4-ylamino)-5-nitropyrimidin-2-yl)-3H-benzo[d]imidazole-5-carbonitrile. The above solid was dissolved in 25 mL 30% (v %) TFA in DCM, then add 0.1 mL triethylsilane. The mixture was stirred for 0.5 hr. HPLC/MS showed one major peak with MH$^+$=422. Yellow residue was obtained after removing the volatiles on rotary evaporator. This residue was suspended in 20 mL 1:1 trimethyl orthoformate: MeOH and stirred for 90 minutes at room temperature. Light yellow solids were precipitated from the orange solution. Titled compound (0.9 g, 99% overall yield) was obtained after filtration.

MS (ESI), m/z 432 ([M+H]$^+$).

3-(5-Amino-4-((R)-8-fluorochroman-4-ylamino)pyrimidin-2-yl)-3H-benzo[d]imidazole-5-carbonitrile. The above solid (0.50 g, 1.1 mmol) was suspended in 50 mL THF, then add the solution of 2.0 g sodium hydrosulfite and 1.5 g sodium bicarbonate in 80 mL water. MeOH (~5 mL) was added to make the mixture homogeneous. After 60 min. stirring, NaCl solid was added to saturate the solution, and the mixture was extracted with EtOAc 3 times. The combined organic solution was dried over Na₂SO₄. Removing the solvents under vacuum afforded 0.26 mg (~60% yield) yellow solid.

MS (ESI), m/z 402 ([M+H]$^+$).

3-(9-((R)-8-fluorochroman-4-yl)-8-(pyrimidin-5-yl)-9H-purin-2-yl)-3H-benzo[d]imidazole-5-carbonitrile. The yellow solution of 20 mg (0.05 mmol) above diamine and 7.6 mg (0.07 mmol) pyrimidine-5-carboxaldehyde (Matrix) in 1.5 mL N,N-dimethylacetamide with 1% (v %) HOAc was heated to 140° C. for 24 hrs. HPLC/MS shows the product as the major peak. Solvents were removed under high vacuum. Preparative HPLC afforded 19 mg (~75%) pale yellow solid as TFA salt of the desired product.

MS (ESI), m/z 490 ([M+H]$^+$).

$^1$H NMR (300 MHz, CDCl₃+5% CD₃OD): δ 9.36 (s, 1H), 9.19 (s, 1H), 9.0-9.1 (m, 3H), 8.65 (s, 1H), 7.80 (d, 1H), 7.58 (d, 1H), 6.95 (t, 1H), 6.63 (q, 1H), 6.38 (d, 1H), 5.9-6.0 (m, 1H), 4.6-4.7 (m, 1H), 4.3-4.4 (m, 1H), 3.0-3.2 (m, 1H), 2.4-2.5 (m, 1H) ppm.

Example B

Synthesis of 3-(8-methyl-9-(tetrahydro-2H-pyran-4-yl)-9H-purin-2-yl)-3H-benzo[d]imidazole-5-carbonitrile

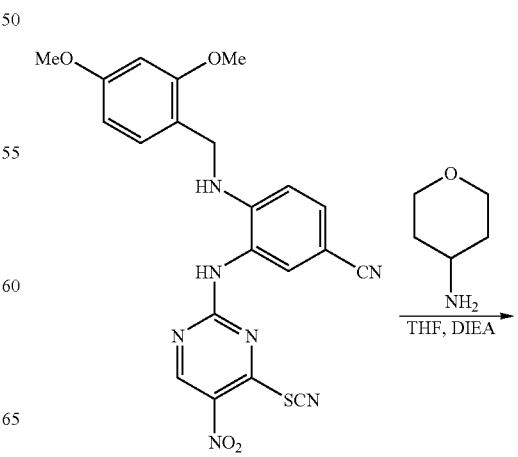

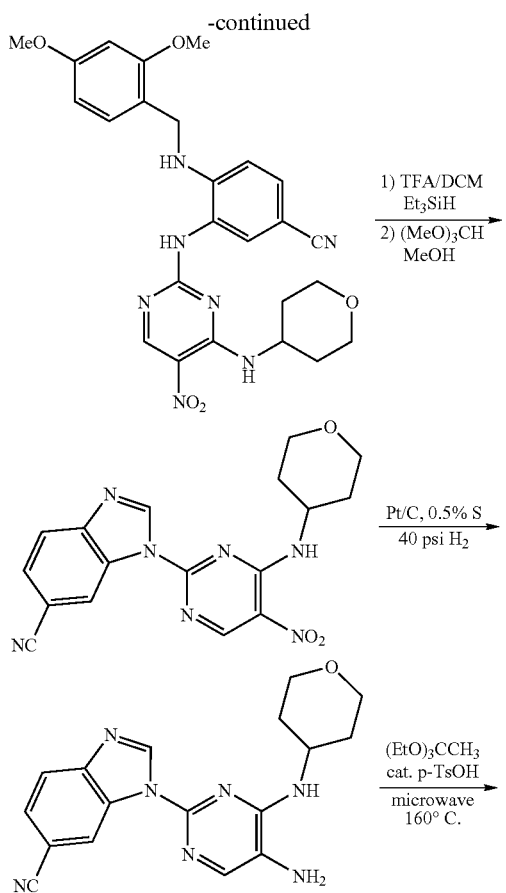

Example 25

4-(2,4-Dimethoxybenzylamino)-3-(5-nitro-4-(tetrahydro-2H-pyran-4-ylamino)pyrimidin-2-ylamino)benzonitrile. To the suspension of 0.92 g (2.0 mmol) of 4-(2,4-dimethoxybenzylamino)-3-(5-nitro-4-thiocyanatopyrimidin-2-ylamino)benzonitrile in 40 mL anhydrous THF was added 0.22 g (2.2 mmol) 4-amino-tetrahydropyran, then 0.7 mL (4.0 mmol) N,N-diisopropylethylamine. The mixture was stirred at room temperature under Argon balloon for 16 hrs till HPLC showed the completion of reaction. The mixture became clear then. The orange-red solution was diluted with EtOAc, washed with brine twice, and then dried over $Na_2SO_4$. Solvents were removed under vacuum to give 1.0 g orange-yellow solid as the crude product.

3-(5-Nitro-4-(tetrahydro-2H-pyran-4-ylamino)pyrimidin-2-yl)-3H-benzo[d]imidazole-5-carbonitrile. The above solid was dissolved in 30 mL 30% (v %) TFA in DCM, then add 0.01 mL triethylsilane. The mixture was stirred for 1 hr. Yellow residue was obtained after removing the volatiles on rotary evaporator. This residue was dissolved in 10 mL 1:1 trimethyl orthoformate: MeOH and the resulting solution were stirred for 60 minutes at room temperature. Yellow solids were precipitated from the orange solution. Desired product (0.70 g, ~95% overall yield) was obtained after filtration.

MS (ESI), m/z 366 ([M+H]$^+$).

3-(5-Amino-4-(tetrahydro-2H-pyran-4-ylamino)pyrimidin-2-yl)-3H-benzo[d]imidazole-5-carbonitrile: In a 250 mL Parr hydrogenation bottle, 3-(5-nitro-4-(tetrahydro-2H-pyran-4-ylamino)pyrimidin-2-yl)-3H-benzo[d]imidazole-5-carbonitrile (0.75 g, 2.0 mmol) was suspended in 40 mL 1:1 EtOAc:MeOH. Platinum, 5% on activated carbon power, sulfide, 0.5% S (as sulfide) (50 mg) was carefully added. The mixture was subjected to an evacuation/fill sequence with hydrogen (repeated 3×), then was hydrogenated under 40 psi for 18 hrs. Filtration through a pad of Celite and concentration of the filtrate gave 0.57 g crude diamine which was carried on without further purification.

MS (ESI), m/z 336 ([M+H]$^+$).

3-(8-Methyl-9-(tetrahydro-2H-pyran-4-yl)-9H-purin-2-yl)-3H-benzo[d]imidazole-5-carbonitrile. To a microwave vial was added 10 mg of the above diamine, a catalytic amount of para-toluene sulfonic acid monohydrate, triethyl orthoacetate (0.5 mL) and EtOH (0.5 mL). The vial was capped and the solution was heated in an Emrys Optimizer microwave at 160° C. for 1 hr. The resulting suspension was filtered, and the solid cake was washed with ACN and MeOH several times to yield 4 mg titled compound as an off white solid.

MS (ESI), m/z 360 ([M+H]$^+$).

$^1$H NMR (300 MHz, $CDCl_3$+5% $CD_3OD$): δ 9.28 (s, 1H), 9.10 (s, 1H), 9.02 (s, 1H), 7.94 (d, 1H), 7.62 (d, 1H), 4.5-4.6 (m, 1H), 4.2-4.3 (m, 2H), 3.6-3.7 (m, 2H), 2.9-3.0 (m, 2H), 2.78 (s, 3H), 1.9-2.0 (m, 2H) ppm.

Example C

Synthesis of 2-(6-fluoro-1H-benzo[d]imidazol-1-yl)-8-(1H-imidazol-2-yl)-9-(tetrahydro-2H-pyran-4-yl)-9H-purine

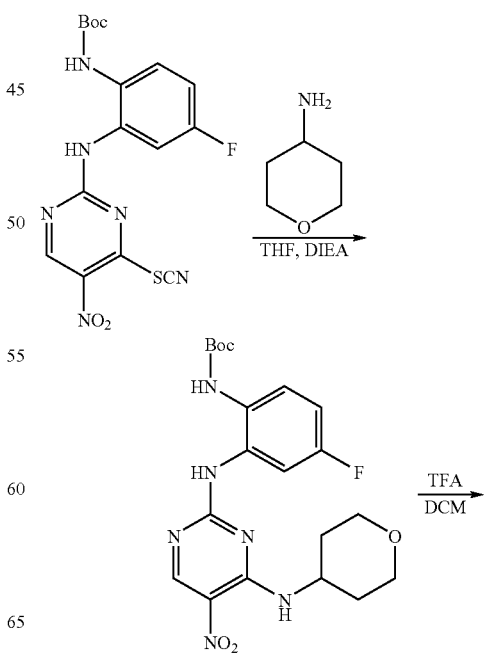

35

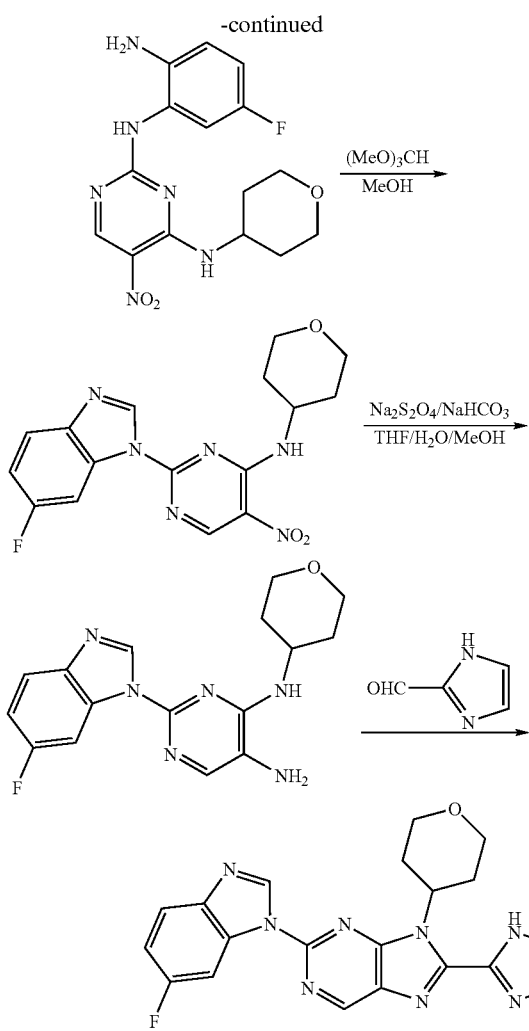

Example 33 tert-Butyl-4-fluoro-2-(5-nitro-4-(tetrahydro-2H-pyran-4-ylamino)pyrimidin-2-ylamino)phenylcarbamate. To the solution of 96 mg (0.95 mmol) of 4-amino-tetrahydropyran in 35 mL anhydrous THF was added 0.35 g (0.86 mmol) tert-butyl 4-fluoro-2-(5-nitro-4-thiocyanatopyrimidin-2-ylamino)phenylcarbamate, then 0.3 mL N,N-diisopropylethyl amine (1.7 mmol). The slightly cloudy mixture was stirred at room temperature for 3 hrs till HPLC showed the completion of reaction. The mixture became clear then. The reaction mixture was diluted with EtOAc, washed with brine twice, and then dried over $Na_2SO_4$. Solvents were removed under vacuum to give 0.28 g (~70% yield) orange-yellow solid as the crude product.

MS (ESI), m/z 449 ([M+H]$^+$).

2-(6-Fluoro-1H-benzo[d]imidazol-1-yl)-5-nitro-N-(tetrahydro-2H-pyran-4-yl)pyrimidin-4-amine. The above solid was dissolved in 25 mL 30% (v %) TFA in DCM. The mixture was stirred for 1 hr. Yellow residue was obtained after removing the volatiles on rotary evaporator. This residue was dissolved in 10 mL 1:1 trimethyl orthoformate: MeOH and the resulting solution were stirred for 30 minutes at room temperature. Orange-yellow solids were precipitated from the orange solution. Titled compound (0.20 g, ~90% yield) was obtained after filtration.

MS (ESI), m/z 359 ([M+H]$^+$).

2-(6-Fluoro-1H-benzo[d]imidazol-1-yl)-N$^4$-(tetrahydro-2H-pyran-4-yl)pyrimidine-4,5-diamine. The above solid was suspended in 40 mL THF, then add the solution of 1.5 g sodium hydrosulfite and 0.75 g sodium bicarbonate in 45 mL water. MeOH (~2 mL) was added to make the mixture homogeneous. After 30 min. stirring, NaCl solid was added to saturate the solution, and the mixture was extracted with EtOAc 3 times. The combined organic solution was dried over $Na_2SO_4$. Removing the solvents under vacuum afforded 145 mg (~80% yield) orange-yellow solid.

MS (ESI), m/z 329 ([M+H]$^+$).

2-(6-Fluoro-1H-benzo[d]imidazol-1-yl)-8-(1H-imidazol-2-yl)-9-(tetrahydro-2H-pyran-4-yl)-9H-purine. The yellow suspension of 12 mg (0.037 mmol) above diamine and 5 mg (0.055 mmol) 2-imidazolecarboxaldehyde in 1 mL N,N-dimethylacetamide with 1% (v %) HOAc was heated to 140° C. for 16 hrs. The suspension became clear orange-yellow solution. HPLC/MS shows the product as the major peak. Solvents were removed under high vacuum. Preparative HPLC afforded 8 mg (~50%) yellow residue as TFA salt of the desired product.

MS (ESI), m/z 405 ([M+H]$^+$).

$^1$H NMR (300 MHz, CDCl$_3$+5% CD$_3$OD): δ 9.28 (s, 1H), 9.02 (s, 1H), 8.4-8.5 (m, 1H), 7.7-7.8 (m, 1H), 7.32 (s, 2H), 7.1-7.2 (m, 1H), 6.4-6.6 (m, 1H), 4.2-4.3 (m, 2H), 3.6-3.8 (m, 2H), 3.0-3.2 (m, 3H), 1.9-2.0 (m, 2H) ppm.

Example D

Synthesis of 8-methyl-9-(tetrahydro-2H-pyran-4-yl)-2-(6-(trifluoromethoxy)-1H-benzo[d]imidazol-1-yl)-9H-purine

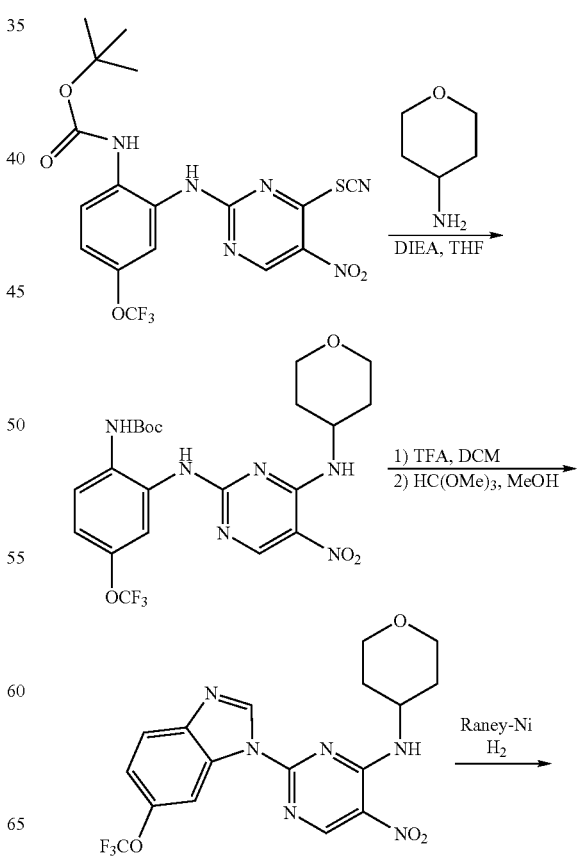

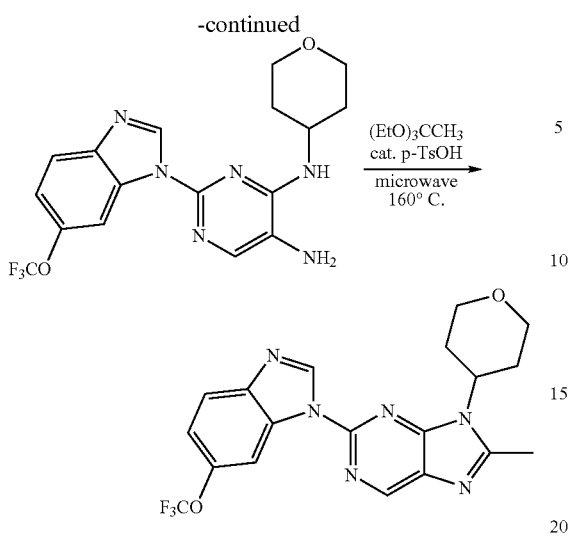

Example 76 tert-Butyl-2-(5-nitro-4-(tetrahydro-2H-pyran-4-ylamino)pyrimidin-2-ylamino)-4-(trifluoromethoxy)phenylcarbamate. tert-Butyl 2-(5-nitro-4-thiocyanatopyrimidin-2-ylamino)-4-(trifluoromethoxy)phenylcarbamate (0.94 g, 2.0 mmol) was dissolved in 40 mL anhydrous THF, then added 0.22 g (2.2 mmol) 4-amino-tetrahydropyran, and 0.7 mL (4.0 mmol) N,N-diisopropylethylamine. The mixture was stirred at room temperature under Argon balloon for 3 hrs till HPLC showed the completion of reaction. The orange-red solution was diluted with EtOAc, washed with brine twice, and then dried over $Na_2SO_4$. Solvents were removed under vacuum to give 1.0 g orange-yellow solid as the crude product.

MS (ESI), m/z 515 ([M+H]$^+$).

5-Nitro-N-(tetrahydro-2H-pyran-4-yl)-2-(6-(trifluoromethoxy)-1H-benzo[d]imidazol-1-yl)pyrimidin-4-amine. A freshly prepared solution of 30% TFA in DCM (25 mL) was added to the 1.0 g tert-Butyl 2-(5-nitro-4-(tetrahydro-2H-pyran-4-ylamino)pyrimidin-2-ylamino)-4-(trifluoromethoxy)phenylcarbamate and the solution were stirred at room temperature for 2 hrs. The solvents were removed in vacuo to yield an orange residue that was carried on without further purification (MH$^+$=415). This residue was dissolved in 20 mL 1:1 trimethyl orthoformate: MeOH and the resulting solution were stirred for 30 minutes at room temperature. Yellow solids were precipitated from the orange solution. Desired product (0.6 g, 70% overall yield) was obtained after filtration.

MS (ESI), m/z 425 ([M+H]$^+$).

N$^4$-(tetrahydro-2H-pyran-4-yl)-2-(6-(trifluoromethoxy)-1H-benzo[d]imidazol-1-yl)pyrimidine-4,5-diamine. To a suspension of 0.36 g 5-nitro-N-(tetrahydro-2H-pyran-4-yl)-2-(6-(trifluoromethoxy)-1H-benzo[d]imidazol-1-yl)pyrimidin-4-amine in 20 mL 1:1 EtOAc:MeOH was added 2 mL Raney-Ni 2800 water slurry. The mixture was subjected to a purge/fill sequence with hydrogen (repeated 3x), and hydrogenated for 18 hr at 50 psi. Filtration through a pad of Celite and concentration of the filtrate gave 0.35 g crude diamine that was carried on without further purification.

MS (ESI), m/z 395 ([M+H]$^+$).

8-Methyl-9-(tetrahydro-2H-pyran-4-yl)-2-(6-(trifluoromethoxy)-1H-benzo[d]imidazol-1-yl)-9H-purine. To a microwave vial was added 15 mg of the above diamine, a catalytic amount of para-toluene sulfonic acid monohydrate, triethyl orthoacetate (0.5 mL) and EtOH (0.5 mL). The vial was capped and the solution was heated in an Emrys Optimizer microwave at 160° C. for 2 hrs. The resulting red solution was concentrated in vacuo and purified by HPLC to yield 9 mg TFA salt of the titled compound as a pale yellow solid.

MS (ESI), m/z 419 ([M+H]$^+$).

$^1$H NMR (300 MHz, CDCl$_3$): δ 9.52 (s, 1H), 9.12 (s, 1H), 8.68 (s, 1H), 7.98 (d, 1H), 7.36 (d, 1H), 4.6-4.7 (m, 1H), 4.2-4.3 (m, 2H), 3.6-3.7 (m, 2H), 2.8-3.0 (m, 2H), 2.82 (s, 3H), 1.8-2.0 (m, 2H) ppm.

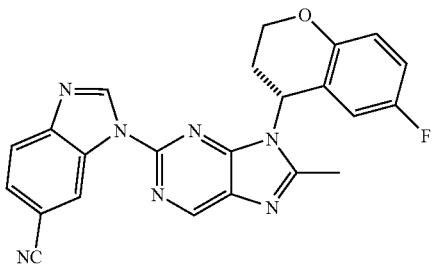

3-(9-((R)-6-Fluorochroman-4-yl)-8-methyl-9H-purin-2-yl)-3H-benzo[d]imidazole-5-carbonitrile. The titled compound was prepared using the standard MW procedure (5 min at 150° C.) and was obtained as a TFA salt after RP-HPLC purification.

$^1$H-NMR (300 MHz, CDCl$_3$+5% CD$_3$OD) δ 9.1 (br s, 1H), 9.0 (s, 1H), 8.6 (s, 1H), 7.9 (d, 1H), 7.6 (d, 1H), 7.2 (dd, 1H), 6.9 (td, 1H), 6.3 (dd, 1H), 5.9 (br t, 1H), 4.6 (m, 1H), 4.4 (t, 1H), 3.0 (m, 1H), 2.7 (s, 3H), 2.4 (m, 1H) ppm; $^{19}$F δ-76, 122 ppm; MH$^+$=426.

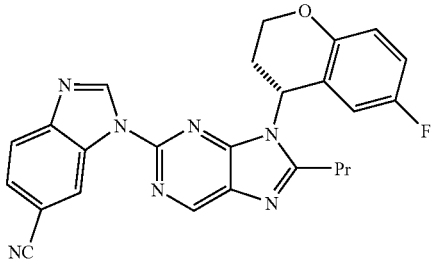

3-(9-((R)-6-fluorochroman-4-yl)-6-methyl-8-propyl-9H-purin-2-yl)-3H-benzo[d]imidazole-5-carbonitrile. The titled compound was prepared using the standard MW procedure with trimethyl orthobutyrate, requiring 30 min at 150° C.

$^1$H-NMR (300 MHz, CDCl$_3$) δ 9.2 (s, 1H), 9.0 (s, 1H), 8.6 (s, 1H), 7.9 (d, 1H), 7.6 (dd, 1H), 7.2 (dd, 1H), 6.9 (td, 1H), 6.3 (dd, 1H), 5.9 (br s, 1H), 4.6 (m, 1H), 4.4 (td, 1H), 3.1-2.9 (m, 3H), 2.4 (m, 1H), 2.0 (q, 2H) 1.1 (t, 3H) ppm; $^{19}$F δ-122 ppm; MH$^+$=454.

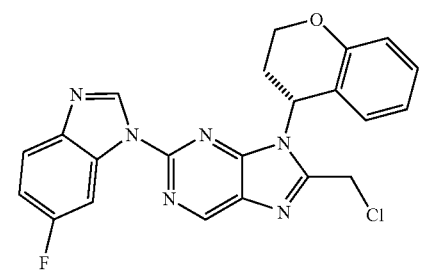

8-(Chloromethyl)-9-((R)-chroman-4-yl)-2-(6-fluoro-1H-benzo[d]imidazol-1-yl)-9H-purine. The titled compound was obtained in low yield (15%) from the microwave reaction (60 min at 150° C.) of N$^4$—((R)-chroman-4-yl)-2-(6-fluoro-1H-benzo[d]imidazol-1-yl)pyrimidine-4,5-diamine (36 mg), 2-chloro-1,1,1-trimethoxyethane (1 mL), a catalytic amount of para-toluene sulfonic acid monohydrate and MeOH (1 mL). The resulting reaction mixture was concentrated in vacuo, and purified via RP-HPLC.

$^1$H-NMR (300 MHz, CDCl$_3$) δ 9.2 (br s, 1H), 9.1 (s, 1H), 8.0 (br s, 1H), 7.8 (m, 2H), 7.2-7.1 (m, 3H), 6.8 (m, 2H), 6.1 (dd, 1H), 4.9 (q, 2H), 4.6 (m, 1H), 4.4 (td, 1H), 3.1 (m, 1H), 2.5 (s, 1H) ppm; $^{19}$F δ −76, −115 ppm; MH$^+$=435/437.

Example E

Synthesis of 2-(1H-benzo[d]imidazol-1-yl)-9-((R)-8-fluorochroman-4-yl)-8-methyl-9H-purine

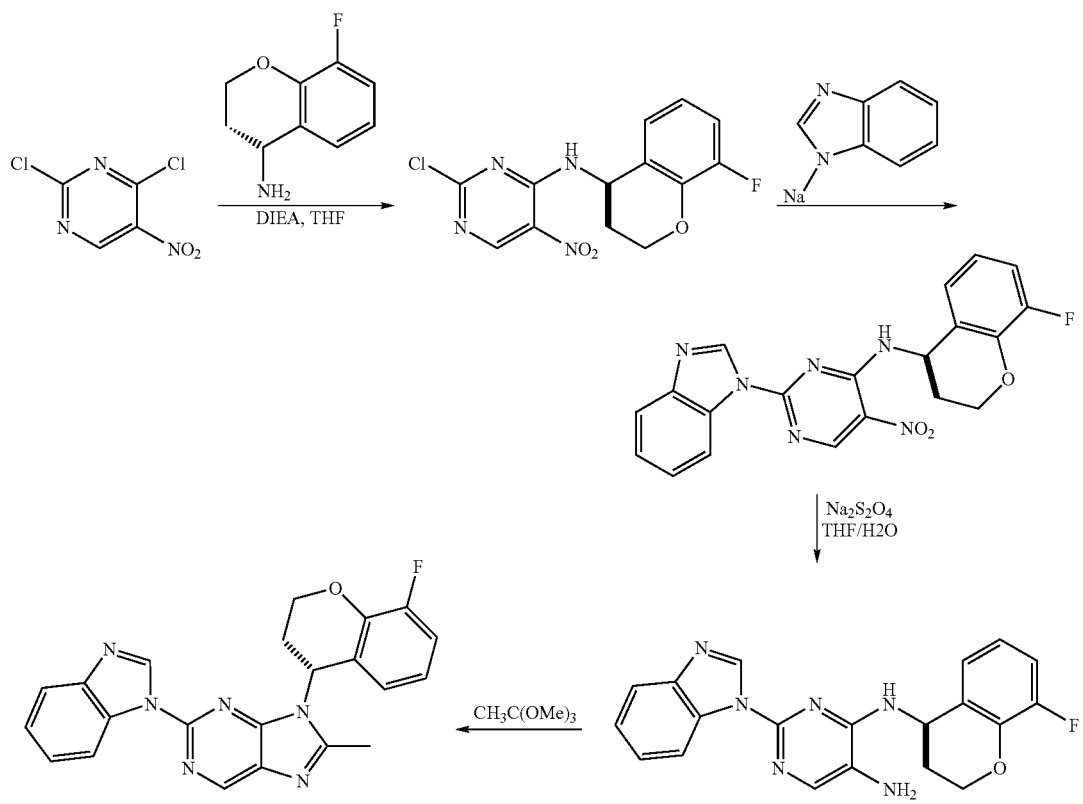

Example 81

2-(1H-Benzo[d]imidazol-1-yl)-N—((R)-8-fluorochroman-4-yl)-5-nitropyrimidin-4-amine. (R)-8-Fluorochroman-4-amine (60 mg) was added to a solution of 2,4-dichloro-5-nitropyrimidine (70 mg) and DIEA (0.14 mL) in THF (5 mL) at −78° C. The reaction mixture was stirred for a further 15 min at −78° C. then removed from the cold bath and allowed to warm to RT. A one molar solution of the sodium salt of benzimidazole (0.7 ml, stock solution prepared via the addition of sodium hydride to a benzimidazole solution in THF) was added to the reaction intermediate ((R)-2-chloro-N-(8-fluorochroman-4-yl)-5-nitropyrimidin-4-amine) and the resulting mixture was stirred at RT overnight. Purification via column chromatography (elution with MeOH/DCM) gave the titled compound (120 mg), MH$^+$=407.

2-(1H-Benzo[d]imidazol-1-yl)-9-((R)-8-fluorochroman-4-yl)-7H-purin-8(9H)-one. A freshly prepared solution of sodium hydrosulfite (tech, 0.5 g) and sodium bicarbonate (0.25 g) in H$_2$O (5 mL) was added to a solution of the above nitro compound (120 mg) in THF (10 mL). The mixture was stirred vigorously for 30 min then extracted with EtOAc (2×) and DCM (2×), the combined organics were washed with brine, dried, filtered and concentrated to yield the intermediate 2-(1H-benzo[d]imidazol-1-yl)-N$^4$—((R)-8-fluorochroman-4-yl)pyrimidine-4,5-diamine that was used as such in the next step.

2-(1H-benzo[d]imidazol-1-yl)-9-((R)-8-fluorochroman-4-yl)-8-methyl-9H-purine. The titled compound was prepared using the standard MW procedure and was obtained as a TFA salt after RP-HPLC purification.

$^1$H-NMR (CH$_3$OD) δ 9.9 (s, 1H), 9.1 (s, 1H), 7.9 (d, 1H), 7.8 (d, 1H), 7.55 (m, 2H), 7.1 (br t, 1H), 6.7 (m, 1H), 6.6 (d, 1H), 6.2 (br t, 1H), 4.6 (m, 1H), 4.5 (m, 1H), 2.9-3.0 (m, 1H), 2.9 (s, 3H), 2.45-2.55 (m, 1H) ppm; MH$^+$=401.

Example F

Synthesis of 2-(1H-benzo[d]imidazol-1-yl)-9-(8-fluoroisochroman-4-yl)-8-phenyl-9H-purine

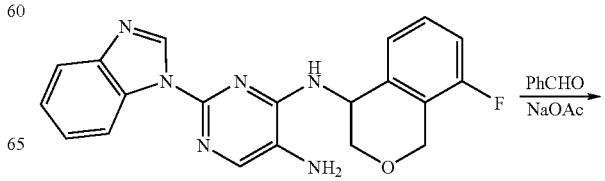

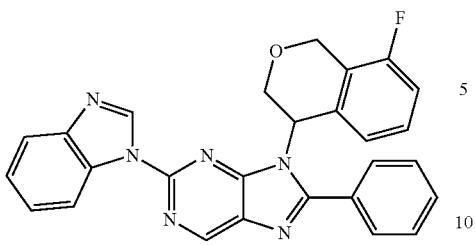
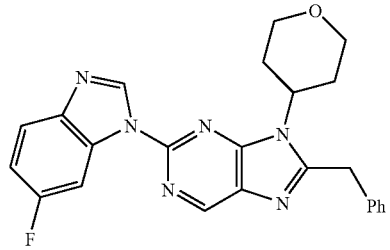

Example 86

2-(1H-benzo[d]imidazol-1-yl)-9-(8-fluoroisochroman-4-yl)-8-phenyl-9H-purine. 2-(1H-benzo[d]imidazol-1-yl)-N⁴-(8-fluoroisochroman-4-yl)pyrimidine-4,5-diamine (synthesized from 8-fluoroisochroman-4-amine via the procedure described in Example E) was refluxed with excess benzaldehyde and sodium acetate for 10 hrs. The titled compound was obtained as a TFA salt after RP-HPLC purification.

¹H-NMR (CH₃OD) δ 9.2 (s, 1H), 7.8-7.9 (br d, 4H), 7.6-7.7 (m, 4H), 7.5 (m, 1H), 7.4 (m, 1H), 7.2 (m, 1H), 7.1 (m, 1H), 6.9 (d, 1H), 6.0 (br t, 1H), 5.0 (br d, 2H), 4.5 (br t, 1H), 4.3-4.4 (m, 1H) ppm; MH⁺=463.

Example G

Synthesis of 8-benzyl-2-(6-fluoro-1H-benzo[d]imidazol-1-yl)-9-(tetrahydro-2H-pyran-4-yl)-9H-purine

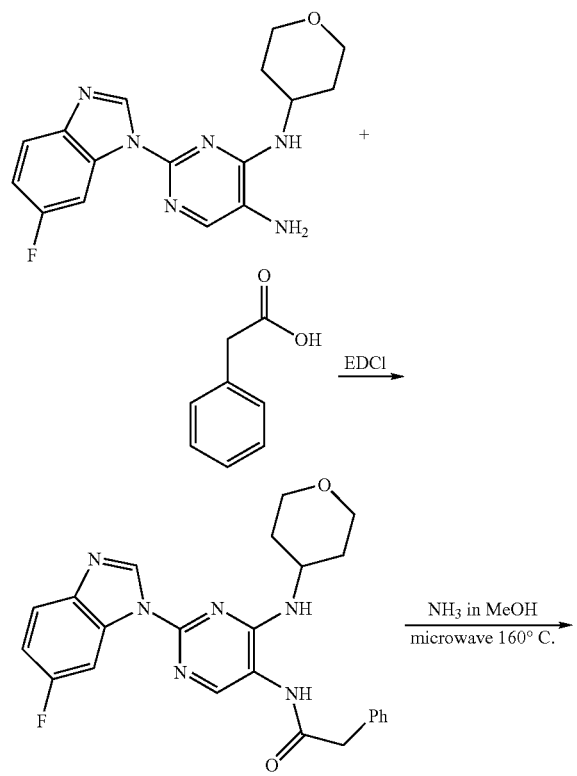

Example 90

N-(2-(6-Fluoro-1H-benzo[d]imidazol-1-yl)-4-(tetrahydro-2H-pyran-4-ylamino)pyrimidin-5-yl)-2-phenylacetamide. To the solution of 10 mg (0.030 mmol) 2-(6-fluoro-1H-benzo[d]imidazol-1-yl)-N⁴-(tetrahydro-2H-pyran-4-yl)pyrimidine-4,5-diamine in 1 mL acetonitrile was added 16 mg (0.12 mmol) of phenylacetic acid and 20 mg (excess) 1-[3-(dimethylamino)propyl]-3-ethylcarbodiimide hydrochloride. The solution was stirred for 1 hr at room temperature. Solvent was removed under vacuum and column chromatography with 5% MeOH in DCM provided 10 mg (75%) pale yellow solid as the desired amide.

MS (ESI), m/z 447 ([M+H]⁺).

8-Benzyl-2-(6-fluoro-1H-benzo[d]imidazol-1-yl)-9-(tetrahydro-2H-pyran-4-yl)-9H-purine. The above yellow solid was dissolved in 1 mL 7N ammonium in MeOH. The solution was heated by microwave to 160° C. for 48 hrs. HPLC/MS shows the product as the major peak. Solvents were removed under vacuum, and column chromatography with 5% MeOH in DCM afforded 4 mg (42%) desired product as a white solid.

MS (ESI), m/z 429 ([M+H]⁺).

¹H NMR (300 MHz, CDCl₃+5% CD₃OD): δ 9.28 (s, 1H), 9.02 (s, 1H), 8.4-8.5 (m, 1H), 7.7-7.8 (m, 1H), 7.32 (s, 2H), 7.1-7.2 (m, 1H), 6.4-6.6 (m, 1H), 4.2-4.3 (m, 2H), 3.6-3.8 (m, 2H), 3.0-3.2 (m, 3H), 1.9-2.0 (m, 2H) ppm.

Example H

Synthesis of (2R)-2-(2-(6-chloro-1H-benzo[d]imidazol-1-yl)-8-methyl-9H-purin-9-yl)-N-(2,2,2-trifluoroethyl)propanamide

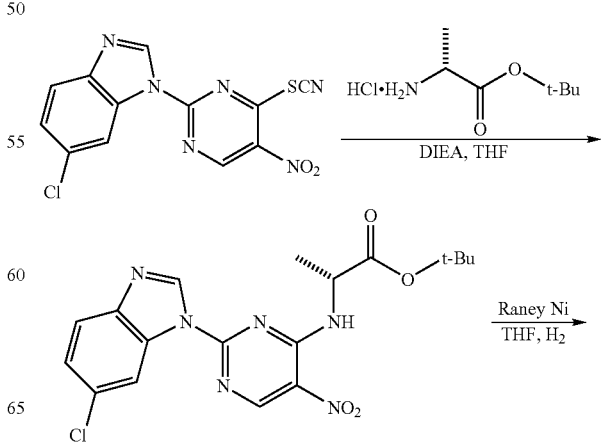

-continued

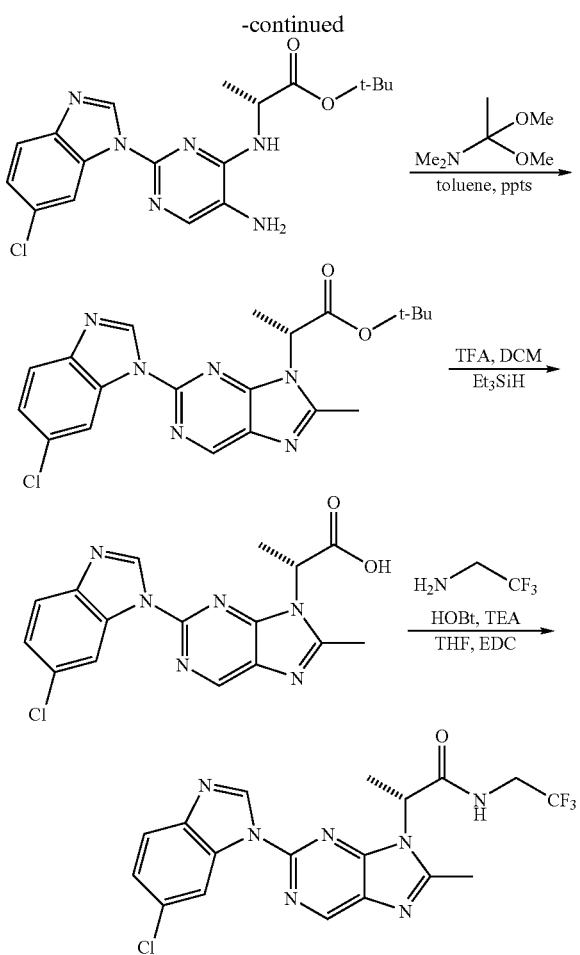

Example 92

(2R)-tert-Butyl 2-(2-(6-chloro-1H-benzo[d]imidazol-1-yl)-5-nitropyrimidin-4-ylamino)propanoate. Diisopropylethylamine (2.6 mL) was added to a mixture of 6-chloro-1-(5-nitro-4-thiocyanatopyrimidin-2-yl)-1H-benzo[d]imidazole (1.66 g, 5 mmol) and D-alanine t-butyl ester hydrochloride (1.1 g, Chem-Impex Int.) in THF (50 mL). The combined mixture was stirred at RT overnight, partitioned between ethyl acetate and water then separated. The aqueous layer was extracted once again with ethyl acetate and the combined organics were concentrated and purified by column chromatography. Elution with DCM and 0.5% MeOH in DCM provided the above compound (0.58 g), MH$^+$=419, 421.

(2R)-tert-Butyl 2-(2-(6-chloro-1H-benzo[d]imidazol-1-yl)-8-methyl-9H-purin-9-yl)propanoate. Under a flush of Ar, a catalytic amount of a Raney Ni solution in water was added to a solution of (2R)-tert-butyl 2-(2-(6-chloro-1H-benzo[d]imidazol-1-yl)-5-nitropyrimidin-4-ylamino)propanoate (50 mg) in THF (10 mL). The flask was closed with a septum, evacuated under house vacuum and hydrogen added via balloon. The resulting suspension was stirred at RT for 2 hr. when the H$_2$ balloon was removed, mixture evacuated and filtered through a plug of celite, that was thoroughly rinsed with THF and MeOH, to yield (2R)-tert-butyl 2-(5-amino-2-(6-chloro-1H-benzo[d]imidazol-1-yl)pyrimidin-4-ylamino)propanoate (MH$^+$=389) that was used as such.

The above diamine was suspended in toluene (1 mL) then N,N-dimethylacetamide dimethyl acetal (25 μL) and pyridinium p-toluenesulfonate (cat.) were added and the mixture was stirred at 100° C. for 24 hr. The reaction was allowed to cool then added directly to a silica gel column that was prepared with 3% MeOH in DCM and eluted with 3 and 4% MeOH in DCM to yield the titled compound (47 mg), MH$^+$=413.

(2R)-2-(2-(6-chloro-1H-benzo[d]imidazol-1-yl)-8-methyl-9H-purin-9-yl)-N-(2,2,2-trifluoroethyl)propanamide. To the above product was added a 30% solution of TFA in DCM (1.5 mL). The solution was stirred for 1 hr when triethylsilane (0.1 mL) was added, stirring was continued overnight, then the solvents were removed under reduced pressure to yield (2R)-2-(2-(6-chloro-1H-benzo[d]imidazol-1-yl)-8-methyl-9H-purin-9-yl)propanoic acid (MH$^+$=357) that was used as such.

1-Hydroxybenzotriazole (25 mg) and triethylamine (40 μL) were sequentially added to the above acid in THF (1 mL). After 5 min N-(3-dimethylaminopropyl)-N'-ethylcarbodiimide hydrochloride (33 mg) and an excess of 2,2,2-trifluoroethanamine were added, the resulting mixture was stirred at RT for 60 hr. The mixture was partition between ethyl acetate and sat. NaHCO$_3$, separated and solvents removed. Purification via column chromatography (5 and 6% MeOH in DCM elution) gave the titled product (26 mg).

MS (ESI), m/z 438 ([M+H]$^+$).
$^1$H-NMR (400 MHz, d$_6$-DMSO) δ 9.2 (s, 1H), 9.1 (s, 1H), 8.8 (t, 1H), 8.6 (d, 1H), 7.8 (d, 1H), 7.4 (dd, 1H), 5.5 (q, 1H), 3.9 (m 2H), 2.6 (s, 3H), 1.8 (d, 3H) ppm.

Example I

Synthesis of 3-(8-(ethylamino)-9-(tetrahydro-2H-pyran-4-yl)-9H-purin-2-yl)-3H-benzo[d]imidazole-5-carbonitrile

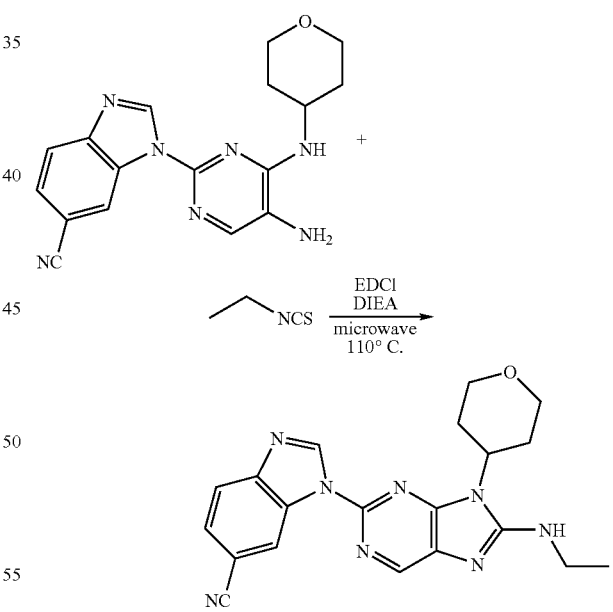

Example 96

In a microwave vial, to the solution of 17 mg (0.050 mmol) 3-(5-amino-4-(tetrahydro-2H-pyran-4-ylamino)pyrimidin-2-yl)-3H-benzo[d]imidazole-5-carbonitrile and 7 microliter ethyl isothiocyanate (0.080 mmol) in 0.5 mL anhydrous dichloromethane was added 29 mg (0.15 mmol) of 1-[3-(dimethylamino)propyl]-3-ethylcarbodiimide hydrochloride and 44 microliter (0.25 mmol) diisopropylethylamine. The vial was capped and the solution was heated in an Emrys Optimizer microwave at 110° C. for 1 to 2 hrs. The resulting red solution was concentrated in vacuo, and purified by HPLC to yield 7 mg TFA salt of the titled compound as an orange yellow solid.

MS (ESI), m/z 389 ([M+H]+).

1H NMR (300 MHz, CDCl3+5% CD3OD): δ 9.3 (s, 1H), 9.0 (s, 1H), 8.7 (s, 1H), 7.9 (d, 1H), 7.6 (d, 1H), 4.6 (m, 1H), 4.2 (m, 2H), 3.5-3.7 (m, 5H), 2.8 (m, 2H), 1.9 (m, 2H), 1.4 (t, 3H) ppm.

Example J

Synthesis of 3-(9-((1R,4R)-4-hydroxy-1,2,3,4-tetrahydronaphthalen-1-yl)-8-methyl-9H-purin-2-yl)-3H-benzo[d]imidazole-5-carbonitrile

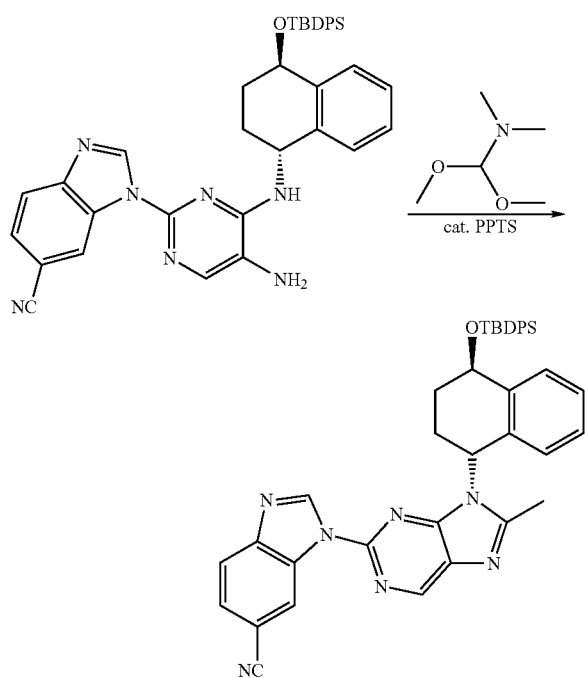

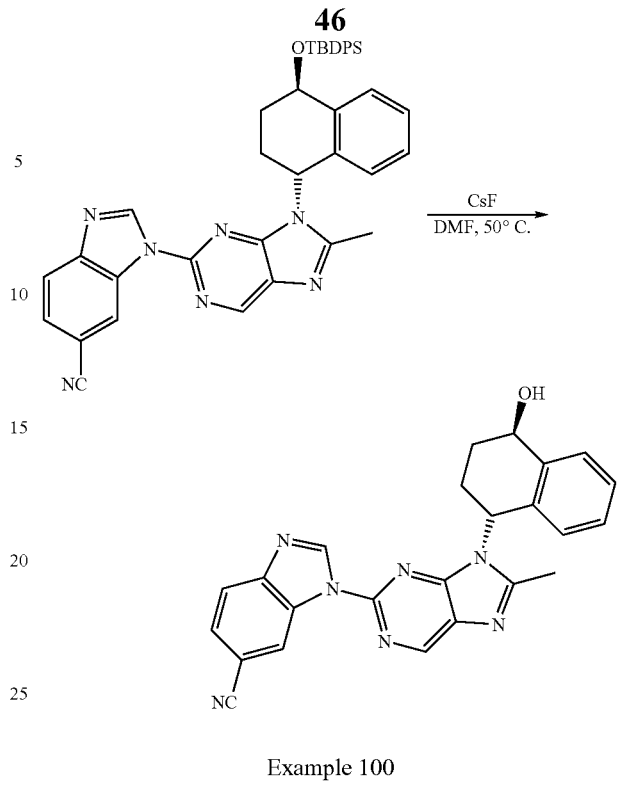

3-(9-((1R,4R)-4-(tert-Butyldiphenylsilyloxy)-1,2,3,4-tetrahydronaphthalen-1-yl)-8-methyl-9H-purin-2-yl)-3H-benzo[d]imidazole-5-carbonitrile. A 50 ml round bottom flask was charged with 0.09 g (0.14 mmol) of 3-(5-amino-4-((1R,4R)-4-(tert-butyldiphenylsilyloxy)-1,2,3,4-tetrahydronaphthalen-1-ylamino)pyrimidin-2-yl)-3H-benzo[d]imidazole-5-carbonitrile (prepared from 3-(5-nitro-4-thiocyanatopyrimidin-2-yl)-3H-benzo[d]imidazole-5-carbonitrile and (1R,4R)-4-(tert-butyldiphenylsilyloxy)-1,2,3,4-tetrahydronaphthalen-1-amine via same procedure as in Example H, step 1 and Example B, step 3). 20 ml of toluene was then added, followed by 0.028 g (0.21 mmol) of N,N-dimethylformamide dimethylacetal, and a catalytic amount of pyridinium p-toluenesulfonate. The resulting mixture was stirred at 100° C. overnight (condenser used with flask). The mixture was cooled to room temp, diluted with 100 ml EtOAc and washed with approx 10 ml water. The organic layer was dried over MgSO4 and concentrated in vacuo, and purified by column chromatography (eluting with 1% MeOH in DCM), to give 0.06 g (65%) of the titled compound. Compound was single peak by HPLC and had an M+H of 660 by MS.

Example 100

3-(9-((1R,4R)-4-Hydroxy-1,2,3,4-tetrahydronaphthalen-1-yl)-8-methyl-9H-purin-2-yl)-3H-benzo[d]imidazole-5-carbonitrile. A 50 ml round bottom flask was charged with 0.06 g (0.091 mmol) of 3-(9-((1R,4R)-4-(tert-butyldiphenylsilyloxy)-1,2,3,4-tetrahydronaphthalen-1-yl)-8-methyl-9H-purin-2-yl)-3H-benzo[d]imidazole-5-carbonitrile. 20 ml of DMF was then added, followed by 0.07 g (0.45 mmol) of Cesium Fluoride, and the resulting mixture was stirred at 50° C. overnight (drying tube was attached to flask). The mixture was cooled to room temp, diluted with 100 ml EtOAc and washed with approx 10 ml water. The organic layer was dried over MgSO4 and concentrated in vacuo, and purified by column chromatography (eluting with 1% MeOH in DCM), to give 0.023 g (60%) of the titled compound.

MS (ESI), m/z 422 ([M+H]+).

1H-NMR (CDCl3) δ 9.1 (s, 1H), 8.9 (s, 1H), 8.3 (s, 1H), 7.9 (d, 1H), 7.8 (d, 1H), 7.5 (d, 1H), 7.3 (t, 1H), 7.0 (t, 1H), 6.5 (d, 1H), 5.8 (q, 1H), 5.3 (q, 1H), 2.7 (m, 4H), 2.5 (m, 1H), 2.3 (m, 1H), 2.0 (q, 1H), 1.6 (br s, 1H) ppm.

Example K

Synthesis of 8-chloro-2-(6-fluoro-1H-benzo[d]imidazol-1-yl)-9-((R)-8-fluorochroman-4-yl)-9H-purine

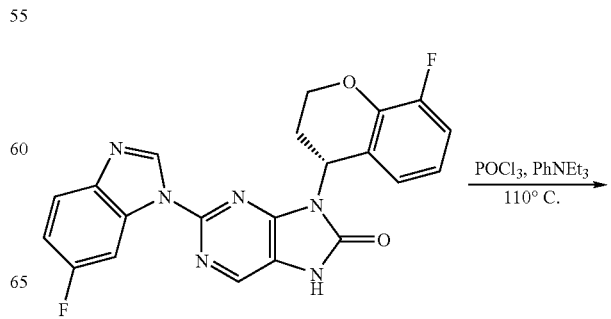

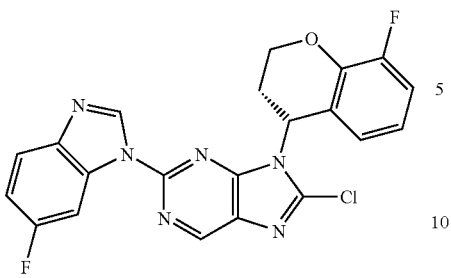

Example 102

In an oven dried flask, to the mixture of 84 mg (0.20 mmol) 2-(6-fluoro-1H-benzo[d]imidazol-1-yl)-9-((R)-8-fluoro-chroman-4-yl)-7H-purin-8(9H)-one (known compound, e.g. WO 2006/108103) in 2 mL phosphorus oxychloride was added 40 microliter N,N-diethylaniline. The yellow suspension was heated in an 110° C. oil bath for 2 days under slow flow of Ar. After concentration in vacuo ice was added to the residue, followed by 4 N NaOH aqueous solution to pH=12, then acidified to pH~1 with concentrated HCl. Extract this aqueous phase with EtOAc excessively, and the combined organic layer was concentrated in vacuo and purified by silica gel column chromatography eluting with DCM and EtOAc to yield 21 mg (24%) the titled compound as a white solid.

MS (ESI), m/z 439 ([M+H]$^+$).

$^1$H NMR (300 MHz, CDCl$_3$): δ 9.0 (s, 1H), 8.9 (s, 1H), 7.7-7.8 (m, 2H), 7.1 (m, 2H), 6.8 (m, 1H), 6.5 (d, 1H), 6.1 (m, 1H), 4.6-4.8 (m, 1H), 4.4 (m, 1H), 3.0 (m, 1H), 2.4 (m, 1H) ppm.

Example L

Synthesis of 2-(6-fluoro-1H-benzo[d]imidazol-1-yl)-9-((R)-8-fluorochroman-4-yl)-8-(6-fluoropyridin-3-yl)-9H-purine

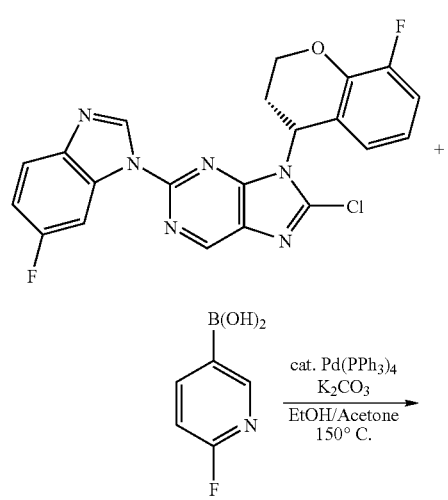

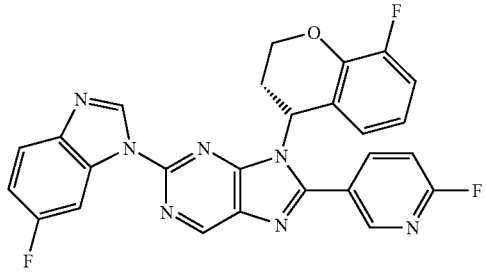

Example 103

In a microwave vial, to the suspension of 15 mg (0.034 mmol) 8-chloro-2-(6-fluoro-1H-benzo[d]imidazol-1-yl)-9-((R)-8-fluorochroman-4-yl)-9H-purine and 9 mg (0.068 mmol) potassium carbonate in 0.5 mL anhydrous acetone, was added 0.2 mL anhydrous alcohol and 9 mg (0.068 mmol) 2-fluoro-5-pyridineboronic acid. The mixture was purged with Ar, and then catalytic amount of tetrakis(triphenylphosphine)palladium(0) (Strem) was added quickly. The vial was capped and the suspension was heated in an Emrys Optimizer microwave at 150° C. for 10 minutes. The resulting brown suspension was concentrated in vacuo, and purified by HPLC to yield 9.4 mg TFA salt of the titled compound as a pale yellow solid.

MS (ESI), m/z 500 ([M+H]$^+$).

$^1$H NMR (300 MHz, CDCl$_3$): δ 9.5 (s, 1H), 9.2 (s, 1H), 8.7 (d, 1H), 8.2 (br t, 1H), 7.9 (m, 1H), 7.7 (br d, 1H), 7.2 (m, 2H), 7.1 (t, 1H), 6.8 (m, 1H), 6.5 (d, 1H), 6.0 (m, 1H), 4.7 (m, 1H), 4.4 (br t, 1H), 3.2 (m, 1H), 2.4 (m, 1H) ppm.

Example M

Synthesis of 4-(2-(6-cyano-1H-benzo[d]imidazol-1-yl)-9-(tetrahydro-2H-pyran-4-yl)-9H-purin-8-ylamino)benzenesulfonamide

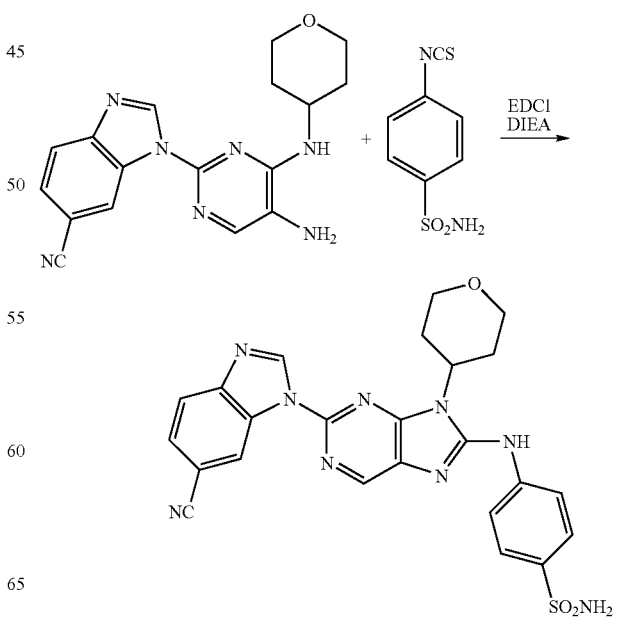

Example 105

To the suspension of 17 mg (0.050 mmol) 3-(5-amino-4-(tetrahydro-2H-pyran-4-ylamino)pyrimidin-2-yl)-3H-benzo[d]imidazole-5-carbonitrile and 16 mg 4-isothiocyanatobenzenesulfonamide (0.076 mmol, Trans World Chemicals) in 0.5 mL anhydrous dichloromethane was added 29 mg (0.15 mmol) of 1-[3-(dimethylamino)propyl]-3-ethylcarbodiimide hydrochloride and 44 microliter (0.25 mmol) diisopropylethylamine. The mixture was stirred at room temperature for 16 hrs. The resulting orange brown suspension was concentrated in vacuo, and purified by HPLC to yield 9.3 mg TFA salt of the titled compound as a pink solid.

MS (ESI), m/z 516 ([M+H]+).

$^1$H NMR (300 MHz, CDCl$_3$+5% CD$_3$OD): δ 9.2 (s, 1H), 9.1 (s, 1H), 8.7 (s, 1H), 7.8-7.9 (m, 5H), 7.6 (m, 1H), 4.7 (m, 1H), 4.2 (m, 2H), 3.6 (t, 2H), 3.0 (m, 2H), 1.9 (m, 2H) ppm.

Example N

Synthesis of 2-(6-fluoro-1H-benzo[d]imidazol-1-yl)-9-((R)-8-fluorochroman-4-yl)-8-(methylthio)-8,9-dihydro-7H-purine

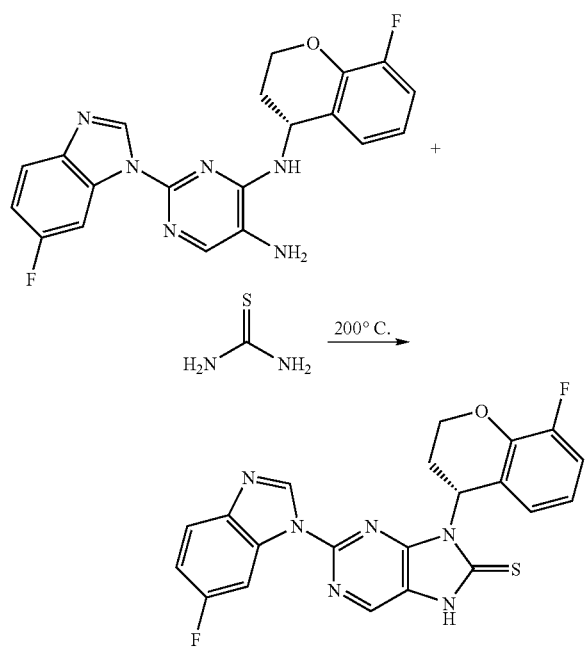

2-(6-Fluoro-1H-benzo[d]imidazol-1-yl)-9-((R)-8-fluorochroman-4-yl)-7H-purine-8(9H)-thione. In a microwave vial, to the solution of 50 mg (0.13 mmol) 2-(6-fluoro-1H-benzo[d]imidazol-1-yl)N$^4$—((R)-8-fluorochroman-4-yl)pyrimidine-4,5-diamine (known compound, e.g. WO 2006/108103) in 0.75 mL anhydrous acetonitrile was added 24 mg (0.32 mmol) thiourea. The vial was capped and the mixture was heated in an Emrys Optimizer microwave at 200° C. for 30 minutes. The resulting red dark suspension was concentrated in vacuo, and partitioned between water and EtOAc. Extract this aqueous phase with EtOAc three more times, and the combined organic layer was concentrated in vacuo, and purified by silica gel column chromatography eluting with DCM and MeOH to yield 8 mg (14%) the titled compound as a pale yellow solid. (Note: On similar diamines, cyclization with 1,1'-thiocarbonyl-diimidazole at 0° C., then slowly warm up to room temperature was found to give improved yields.)

MS (ESI), m/z 437 ([M+H]+).

$^1$H NMR (300 MHz, CDCl$_3$+5% CD$_3$OD): δ 8.7 (s, 1H), 8.4 (s, 1H), 7.7 (m, 1H), 7.5 (m, 1H), 7.0-7.1 (m, 2H), 6.5-6.7 (m, 3H), 4.6 (m, 1H), 4.4 (m, 1H), 2.9 (m, 1H), 2.3 (m, 1H) ppm.

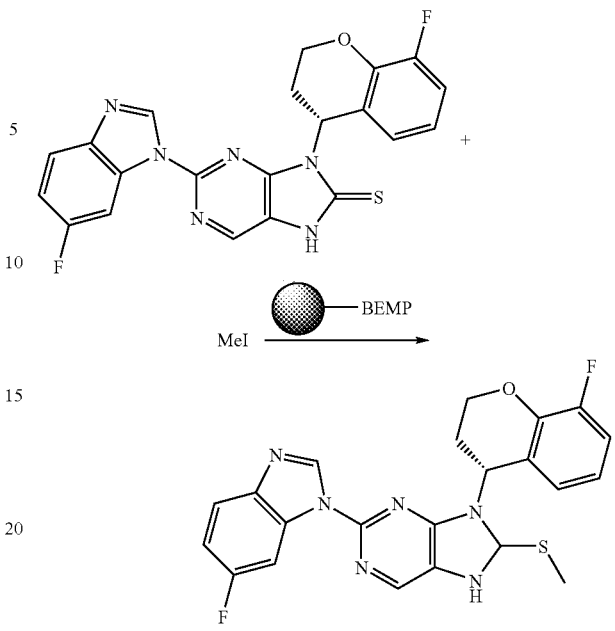

Example 111

2-(6-Fluoro-1H-benzo[d]imidazol-1-yl)-9-((R)-8-fluorochroman-4-yl)-8-(methylthio)-8,9-dihydro-7H-purine. 2-(6-Fluoro-1H-benzo[d]imidazol-1-yl)-9-((R)-8-fluorochroman-4-yl)-7H-purine-8(9H)-thione (4 mg, 0.009 mmol) was dissolved in 1 mL anhydrous acetonitrile, add 25 mg (0.054 mmol) 2-tert-butylimino-2-diethylamino-1,3-dimethyl-perhydro-1,3,2-diazaphosphorine on polystyrene (Fluka), then 3 microliter iodomethane. The mixture was stirred at room temperature for 30 minutes. After concentration in vacuo, the residue was purified by silica gel column chromatography eluting with 2% MeOH in DCM and EtOAc to yield 2.1 mg (52%) the titled compound as a pale yellow solid.

MS (ESI), m/z 451 ([M+H]+).

$^1$H NMR (300 MHz, CDCl$_3$): δ 8.9 (s, 2H), 7.9 (m, 1H), 7.7 (m, 1H), 7.1 (m, 2H), 6.8 (q, 1H), 6.6 (d, 1H), 6.0 (m, 1H), 4.7 (m, 1H), 4.5 (m, 1H), 3.0 (m, 1H), 2.8 (s, 3H), 2.4 (m, 1H) ppm.

Example O

Synthesis of (1R,4R)-4-(2-(6-fluoro-1H-benzo[d]imidazol-1-yl)-8-(pyrimidin-5-yl)-9H-purin-9-yl)-1,2,3,4-tetrahydronaphthalen-1-ol

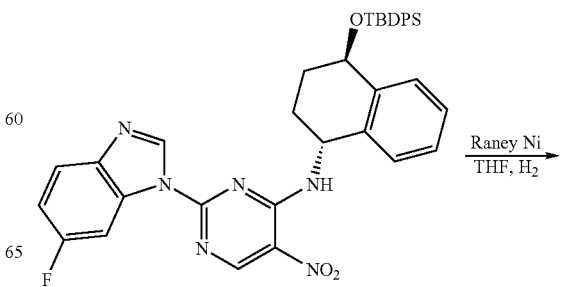

-continued

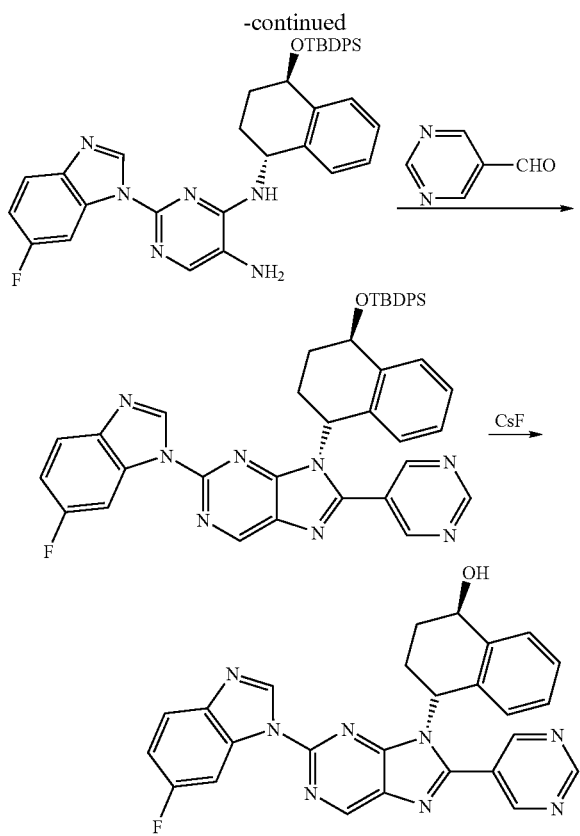

Example 112

N⁴-((1R,4R)-4-(tert-Butyldiphenylsilyloxy)-1,2,3,4-tetrahydronaphthalen-1-yl)-2-(6-fluoro-1H-benzo[d]imidazol-1-yl)pyrimidine-4,5-diamine. Under a flush of Ar, a catalytic amount of a Raney Ni solution in water was added to a solution of 150 mg (0.27 mmol) N-((1R,4R)-4-(tert-butyldiphenylsilyloxy)-1,2,3,4-tetrahydronaphthalen-1-yl)-2-(6-fluoro-1H-benzo[d]imidazol-1-yl)-5-nitropyrimidin-4-amine (prepared from 6-fluoro-1-(5-nitro-4-thiocyanatopyrimidin-2-yl)-1H-benzo[d]imidazole and (1R,4R)-4-(tert-butyldiphenylsilyloxy)-1,2,3,4-tetrahydronaphthalen-1-amine via same procedure as in Example H, step 1) in THF (10 mL). The flask was evacuated under house vacuum and then filled with hydrogen via a balloon. This procedure was repeated 3 times. The resulting suspension was stirred at room temperature for 16 hrs under the H₂ balloon. LCMS indicated the completion of the reduction, and the mixture was filtered through a plug of celite, that was thoroughly rinsed with THF and MeOH. The filtrate was concentrated in vacuo to yield the 130 mg (78%) desired diamine (MH⁺=629) as a white solid that was used as such.

9-((1R,4R)-4-(tert-Butyldiphenylsilyloxy)-1,2,3,4-tetrahydronaphthalen-1-yl)-2-(6-fluoro-1H-benzo[d]imidazol-1-yl)-8-(pyrimidin-5-yl)-9H-purine. In a microwave vial, to the solution of 50 mg (0.080 mmol) the above diamine in 1 mL anhydrous DMF was added 10 mg (0.096 mmol) pyrimidine-5-carboxaldehyde (Matrix) and 100 mg FeCl₃ on silica gel (15% wt). The vial was capped and the mixture was heated in an Emrys Optimizer microwave at 150° C. for 3 hrs. Water was then added to the mixture, and this aqueous phase was extracted with EtOAc three times. The combined organic layer was concentrated in vacuo, and purified on 1000 micron silica gel plate developing with 0.8% MeOH in 1:1 DCM: EtOAc to yield 13 mg (23%) the titled compound as a yellow solid. MS (ESI), m/z 717 ([M+H]⁺).

(1R,4R)-4-(2-(6-Fluoro-1H-benzo[d]imidazol-1-yl)-8-(pyrimidin-5-yl)-9H-purin-9-yl)-1,2,3,4-tetrahydronaphthalen-1-ol. In a small vial, the above purine (13 mg, 0.018 mmol) was dissolved in 1 ml anhydrous DMF, then added 15 mg (0.10 mmol) of Cesium Fluoride, and the resulting mixture was capped and stirred at 50° C. for overnight. The mixture was then cooled to room temp, quenched with water, extracted with DCM three times. The combined organic layer was concentrated in vacuo, and purified by column chromatography (eluting with 0.5% to 5% MeOH in 1:1 DCM: EtOAC) to give 5.3 mg (62%) of the titled compound.

MS (ESI), m/z 479 ([M+H]⁺).

¹H-NMR (CDCl₃) δ 9.4 (s, 1H), 9.2 (d, 2H), 9.0 (s, 1H), 7.9 (d, 1H), 7.7 (m, 1H), 7.5 (d, 1H), 7.4 (t, 1H), 7.0-7.2 (m, 3H), 6.7 (d, 1H), 5.8 (q, 1H), 5.3 (q, 1H), 2.9 (q, 1H), 2.5 (m, 1H), 2.4 (m, 1H), 2.2 (d, 1H), 1.9 (m, 1H) ppm.

Jak3 Kinase Assay

Human Jak3 cDNA was amplified by PCR. A fragment encoding the catalytic domain of Jak3 (508aa to 1124aa) was ligated with GST at 5' end. This fused GST-Jak3 DNA fragment was cloned into the EcoRI site of the donor plasmid pFastBac 1 (Life Technologies #10359-016). The transformation, transposition, and transfection of insect cells (Sf9) were performed according to the manufacture's instructions. The cell lysate containing recombinant GST-Jak3 was used in the kinase assay. Anti-GST antibody (10 μg/ml, Sigma #G1417) was coated onto a 384-well plate at 4° C. overnight. Cell lysate containing GST-Jak3 (1:100 dilution) was added to the anti-GST coated plates, and GST-Jak3 was captured by immobilized anti-GST antibody. Testing compounds and substrate mix (50 mM HEPES, pH 7, 0.5 mM Na₃VO₄, 25 mM MgCl₂, 1 mM DTT, 0.005% BSA, 1 μM ATP, and 4.5 μg/ml biotinyl poly-Glu, Ala, Tyr) were added to the plate to initiate the reaction. After a 60-min incubation, the reaction was stopped by 4 mM EDTA, and phosphorylation of biotinyl poly-Glu, Ala, Tyr was detected using 17 μg/ml Cy5-streptavidin (Amersham, #PA92005) and 2.7 μg/ml Europium-conjugated anti-phosphotyrosine antibody (PerkinElmer #AD0069) using homogeneous time-resolved fluorescence (HTRF) technology.

Jak3 Cellular Assay

The mouse F7 pre-B lymphocyte cell line was used for the cellular Jak3 assay. Human IL-2Rβc cDNA is stably expressed in F7 cells (Kawahara et al., 1995). F7 cells were maintained in RPMI 1640 medium supplemented with 10% fetal bovine serum plus IL-3. Cells (30,000 cells/well) in serum-free medium were seeded in 96-well plates for the cell proliferation assay. Testing compounds were added to cells, followed by the addition of IL-2 (final 20 ng/ml). After a 24-h incubation, the number of viable cells was determined by the CellTiter-Glo Luminescent Cell Viability Assay kit (Promega, #G7573) according to the manufacturer's instructions.

IL-2-Induced IFN-γ Production in the Mouse

Administration of IL-2 leads to an increase in serum IFN-γ in the mouse due to NK secretion of the cytokine (Thornton S, Kuhn K A, Finkelman F D and Hirsch R. NK cells secrete high levels of IFN-γ in response to in vivo administration of IL-2. Eur J Immunol 2001 31:3355-3360). The experiment is carried out essentially according to the protocol in Thornton et al. and the test compounds are administered in order to determine the level of inhibition attained. In summary, female BALB/c mice are fasted for 12-18 hours before a study but have free access to water at all times. Test compounds are administered by gavage one hour before intraperitoneal injection of IL-2 and capture antibody. At termination of the studies, the mice are sacrificed by carbon dioxide inhalation, terminal blood samples are collected by cardiac puncture and serum is generated. Serum is stored frozen until assayed for IFN-γ, as described by the kit manufacturer (BD Pharmingen™, San Diego, Calif.). Using this method Examples 13 and 6 were shown to inhibit IFN-γ production by 76 and 93% respectively on oral dose at 30 mg/kg.

Some comparative examples are shown below. All of the IC$_{50}$'s for Jak3 are below 10 μM.

| Chemistry | Jak 3 (Converted) | Synthetic Route | Example Number |
|---|---|---|---|
| 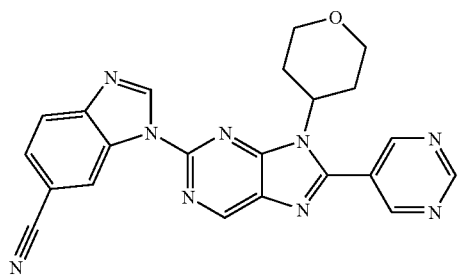 | 1 | A | 1 |
| 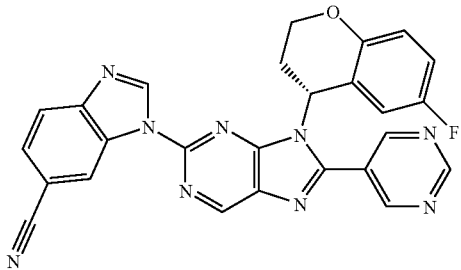 | 1 | A | 2 |
| 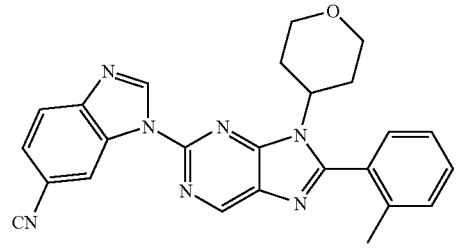 | 2 | A | 3 |
| 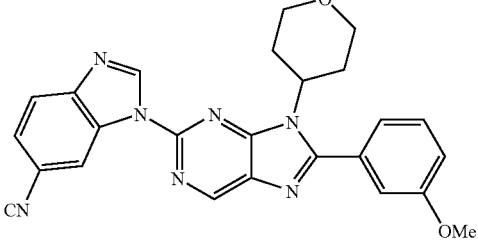 | 2 | A | 4 |
| 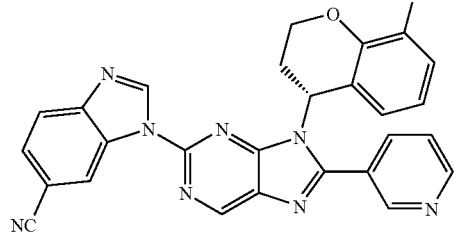 | 1 | A | 5 |

-continued
| Chemistry | Jak 3 (Converted) | Synthetic Route | Example Number |
|---|---|---|---|
| 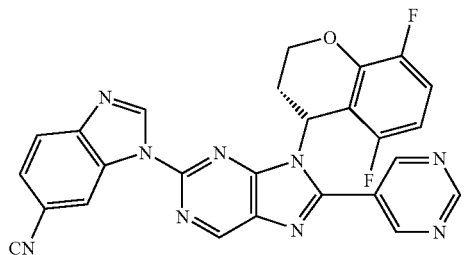 | 1 | A | 6 |
| | 1 | A | 7 |
| | 1 | A | 8 |
| | 1 | A | 9 |
| | 1 | A | 10 |

-continued

| Chemistry | Jak 3 (Converted) | Synthetic Route | Example Number |
|---|---|---|---|
| | 1 | A | 11 |
| | 2 | A | 12 |
| | 1 | A | 13 |
| | 1 | A | 14 |
| | 1 | A | 15 |

-continued
| Chemistry | Jak 3 (Converted) | Synthetic Route | Example Number |
|---|---|---|---|
| 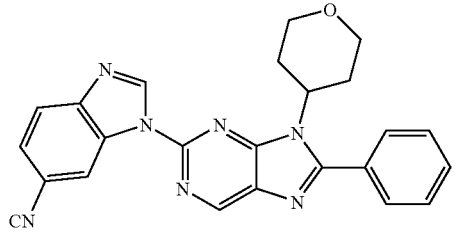 | 1 | A | 16 |
| 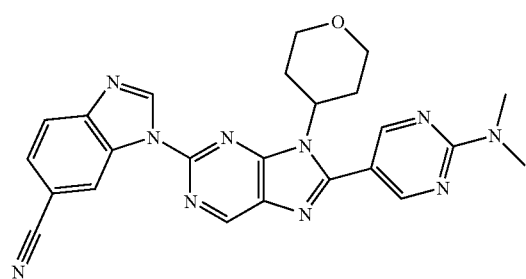 | 1 | A | 17 |
| 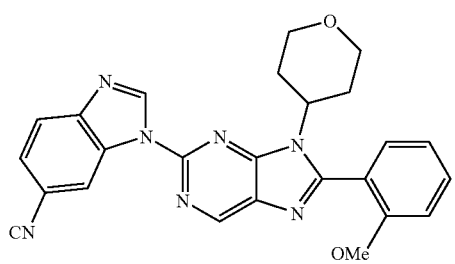 | 2 | A | 18 |
| 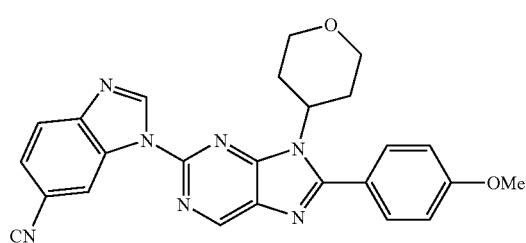 | 2 | A | 19 |
| 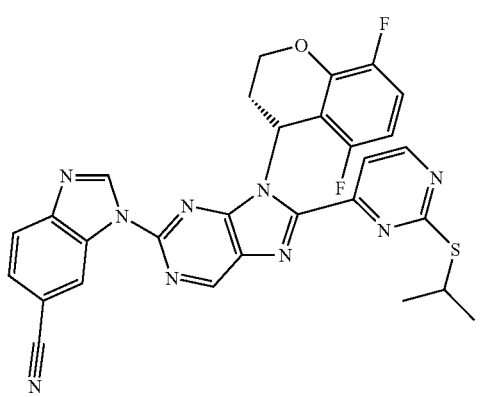 | 2 | A | 20 |

-continued

| Chemistry | Jak 3 (Converted) | Synthetic Route | Example Number |
|---|---|---|---|
| (structure) | 2 | B | 21 |
| (structure) | 1 | B | 22 |
| (structure) | 2 | B | 23 |
| (structure) | 1 | B | 24 |
| (structure) | 1 | B | 25 |

-continued

| Chemistry | Jak 3 (Converted) | Synthetic Route | Example Number |
|---|---|---|---|
| (structure) | 2 | B | 26 |
| (structure) | 2 | C | 27 |
| (structure) | 2 | C | 28 |
| (structure) | 2 | C | 29 |

-continued

| Chemistry | Jak 3 (Converted) | Synthetic Route | Example Number |
|---|---|---|---|
| | 2 | C | 30 |
| | 2 | C | 31 |
| | 1 | C | 32 |
| | 2 | C | 33 |
| | 1 | C | 34 |

-continued

| Chemistry | Jak 3 (Converted) | Synthetic Route | Example Number |
|---|---|---|---|
| | 1 | C | 35 |
| | 1 | C | 36 |
| | 1 | C | 37 |
| | 1 | C | 38 |
| | 1 | C | 39 |

-continued
| Chemistry | Jak 3 (Converted) | Synthetic Route | Example Number |
|---|---|---|---|
| 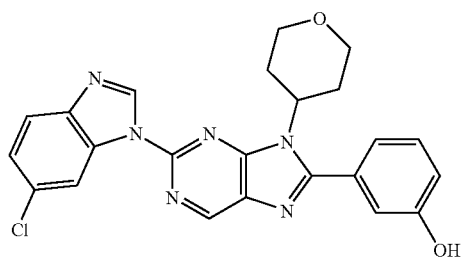 | 1 | C | 40 |
| 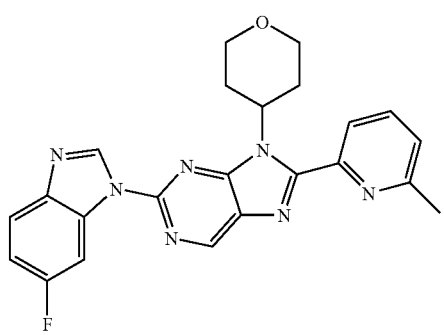 | 3 | C | 41 |
| 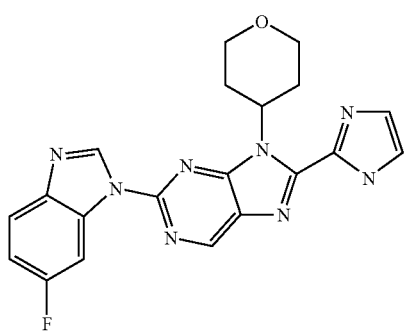 | 2 | C | 42 |
| 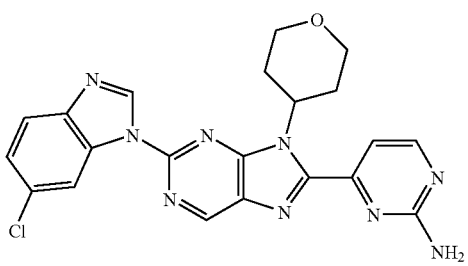 | 1 | C | 43 |
| 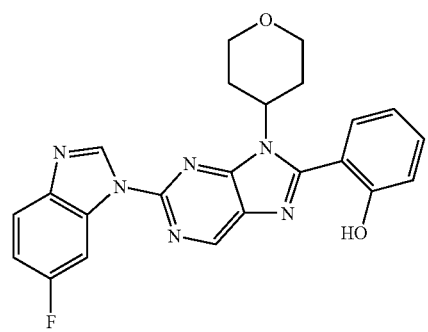 | 2 | C | 44 |

-continued

| Chemistry | Jak 3 (Converted) | Synthetic Route | Example Number |
|---|---|---|---|
| | 1 | C | 45 |
| | 1 | C | 46 |
| | 1 | C | 47 |
| | 2 | C | 48 |
| | 1 | C | 49 |

-continued

| Chemistry | Jak 3 (Converted) | Synthetic Route | Example Number |
|---|---|---|---|
| | 2 | C | 50 |
| | 1 | C | 51 |
| | 2 | C | 52 |
| | 1 | C | 53 |
| | 2 | C | 54 |

-continued

| Chemistry | Jak 3 (Converted) | Synthetic Route | Example Number |
|---|---|---|---|
| | 1 | C | 55 |
| | 3 | C | 56 |
| | 3 | C | 57 |
| | 3 | C | 58 |
| | 1 | C | 59 |

-continued

| Chemistry | Jak 3 (Converted) | Synthetic Route | Example Number |
|---|---|---|---|
| | 2 | C | 60 |
| | 2 | C | 61 |
| | 1 | C | 62 |
| | 1 | C | 63 |
| | 2 | C | 64 |

-continued

| Chemistry | Jak 3 (Converted) | Synthetic Route | Example Number |
|---|---|---|---|
| (structure) | 1 | C | 65 |
| (structure) | 2 | C | 66 |
| (structure) | 2 | C | 67 |
| (structure) | 2 | C | 68 |
| (structure) | 1 | C | 69 |

-continued

| Chemistry | Jak 3 (Converted) | Synthetic Route | Example Number |
|---|---|---|---|
| | 1 | C | 70 |
| | 1 | C | 71 |
| | 1 | D | 72 |
| | 2 | D | 73 |
| | 1 | D | 74 |

-continued
| Chemistry | Jak 3 (Converted) | Synthetic Route | Example Number |
|---|---|---|---|
| 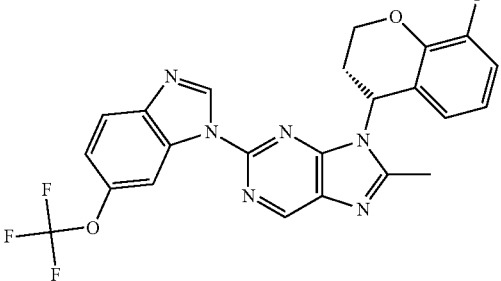 | 2 | D | 75 |
| 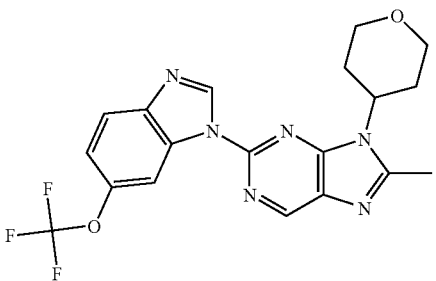 | 1 | D | 76 |
| 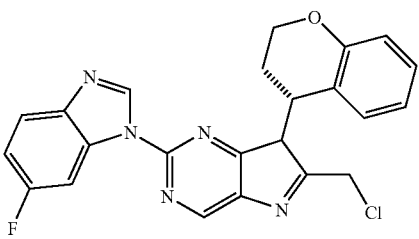 | 1 | D | 77 |
| 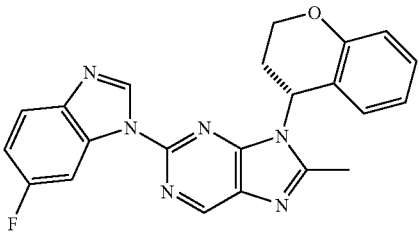 | 1 | D | 78 |
| 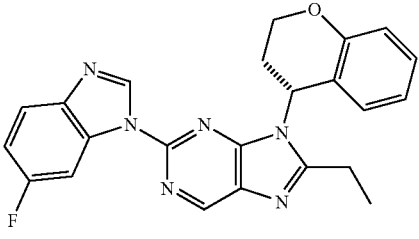 | 1 | D | 79 |
| 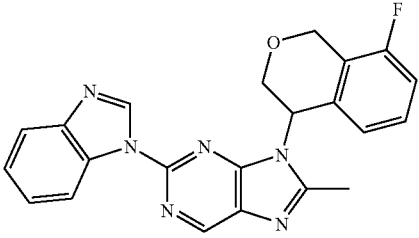 | 2 | E | 80 |

-continued
| Chemistry | Jak 3 (Converted) | Synthetic Route | Example Number |
|---|---|---|---|
| 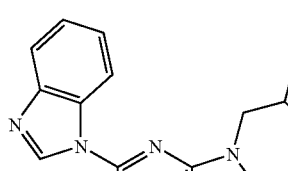 | 1 | E | 81 |
| 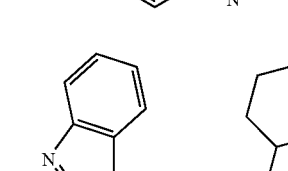 | 3 | E | 82 |
| 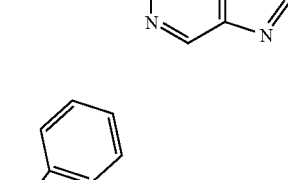 | 1 | E | 83 |
| 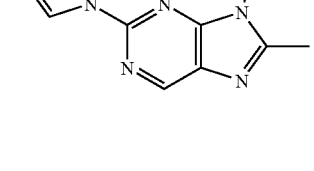 | 3 | E | 84 |
| 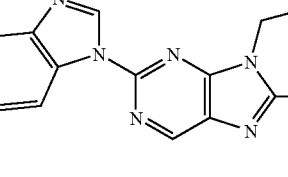 | 3 | F | 85 |
|  | 3 | F | 86 |

-continued
| Chemistry | Jak 3 (Converted) | Synthetic Route | Example Number |
|---|---|---|---|
| 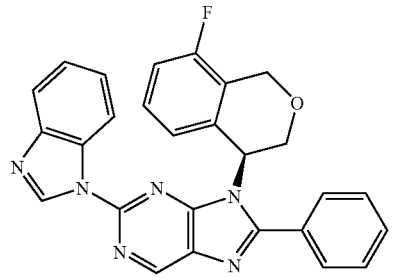 | 2 | F | 87 |
| 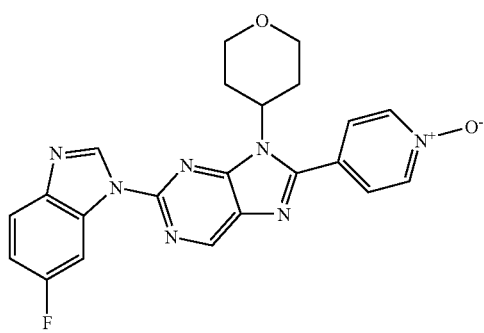 | 2 | F | 88 |
| 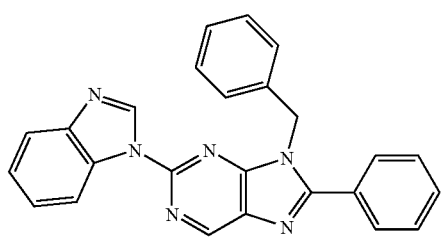 | 3 | F | 89 |
| 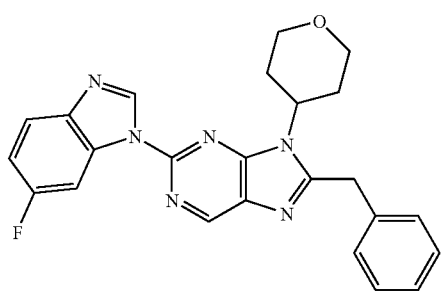 | 2 | G | 90 |
| 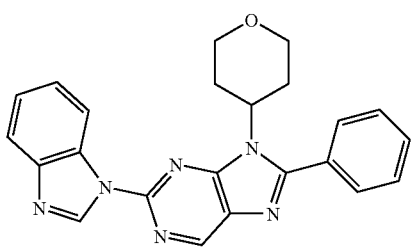 | 2 | G | 91 |

-continued
| Chemistry | Jak 3 (Converted) | Synthetic Route | Example Number |
|---|---|---|---|
| 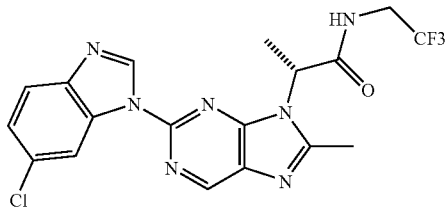 | 1 | H | 92 |
| 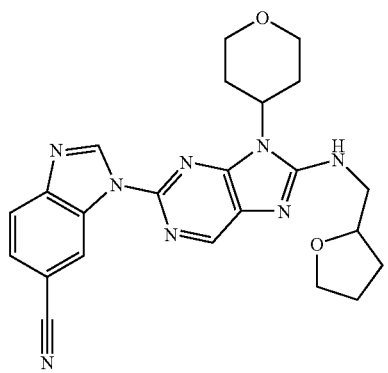 | 1 | I | 93 |
| 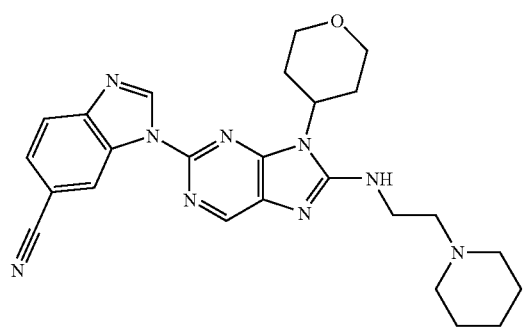 | 1 | I | 94 |
| 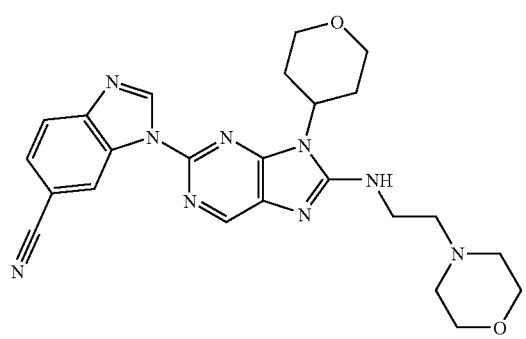 | 1 | I | 95 |
| 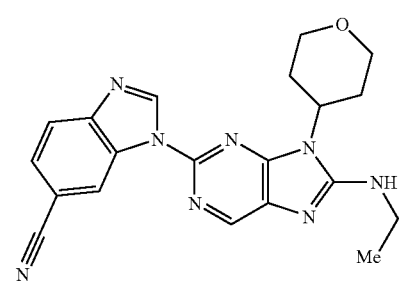 | 1 | I | 96 |

-continued

| Chemistry | Jak 3 (Converted) | Synthetic Route | Example Number |
|---|---|---|---|
| (structure) | 1 | I | 97 |
| (structure) | 1 | I | 98 |
| (structure) | 2 | J | 99 |
| (structure) | 1 | J | 100 |
| (structure) | 1 | K | 101 |

| Chemistry | Jak 3 (Converted) | Synthetic Route | Example Number |
|---|---|---|---|
| 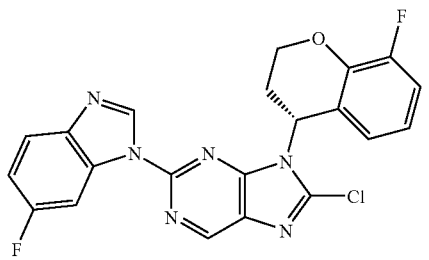 | 1 | K | 102 |
| 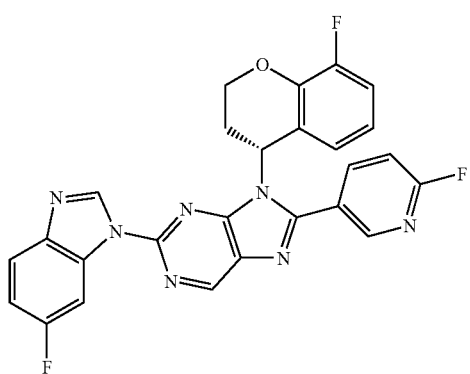 | 1 | L | 103 |
| 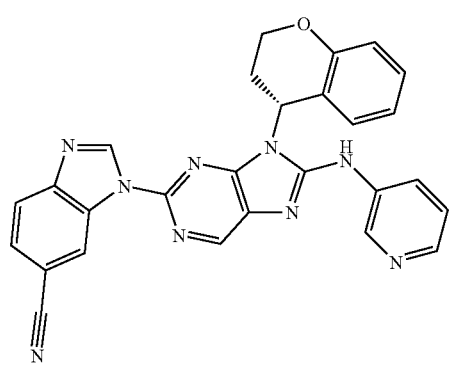 | 1 | M | 104 |
| 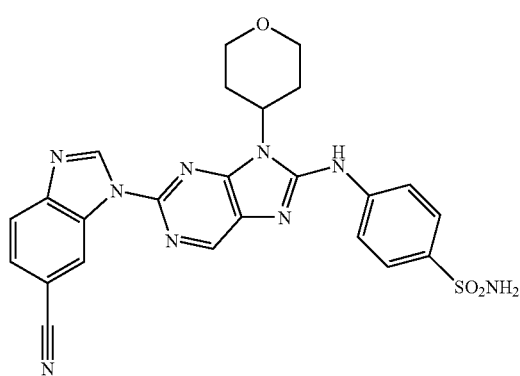 | 1 | M | 105 |

-continued
| Chemistry | Jak 3 (Converted) | Synthetic Route | Example Number |
|---|---|---|---|
| 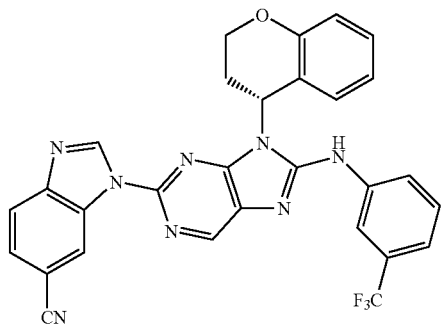 | 2 | M | 106 |
| 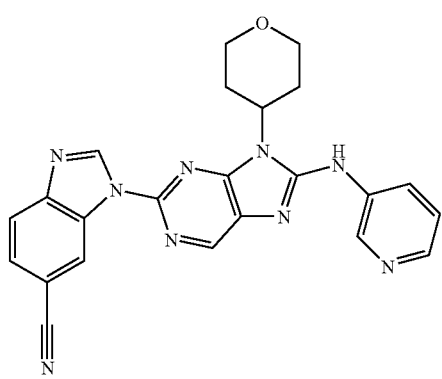 | 1 | M | 107 |
| 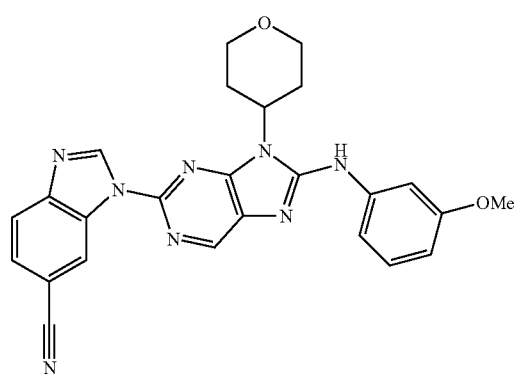 | 1 | M | 108 |
| 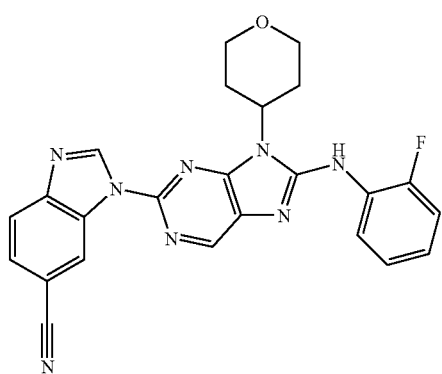 | 1 | M | 109 |

-continued

| Chemistry | Jak 3 (Converted) | Synthetic Route | Example Number |
|---|---|---|---|
| 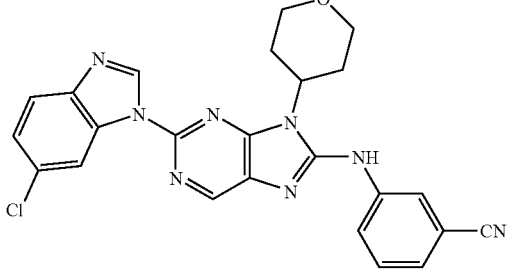 | 3 | M | 110 |
| 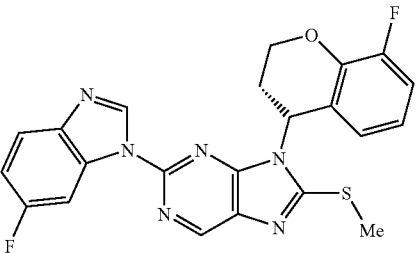 | 1 | N | 111 |
| 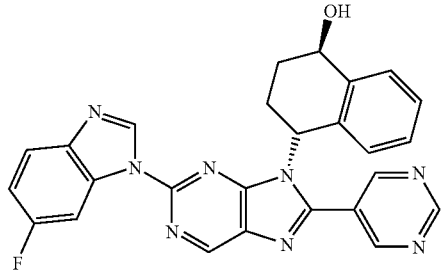 | 1 | O | 112 |

In the foregoing table, an $IC_{50}$ less than 100 nM is represented as 1; an $IC_{50}$ between 100 nM and 1 µM is represented as 2; and an IC 50 greater than 1 µM is represented as 3.

We claim:

1. A compound of formula I

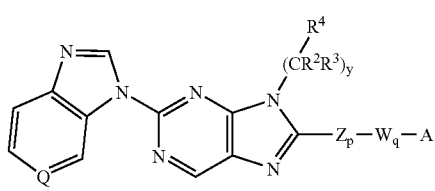

wherein

Q is selected from the group consisting of CX and nitrogen;

X is selected from the group consisting of hydrogen, halogen and an electron-withdrawing group;

Z is selected from the group consisting of oxygen, sulfur, and $NR^2$;

p is zero or one;

A is chosen from the group consisting of alkyl, pyridinyl, pyrimidinyl, benzimidazolyl, imidazolyl, furanyl, pyrrolyl, thiazolyl, quinolinyl, morpholinyl, cyclopentyl, aryl, substituted alkyl, substituted pyridinyl, substituted pyrimidinyl, substituted benzimidazolyl, substituted imidazolyl, substituted furanyl, substituted pyrrolyl, substituted thiazolyl, substituted quinolinyl, substituted morpholinyl, substituted cyclopentyl, substituted aryl, cyano and halogen;

W is $(C_1-C_6)$alkylene;

q is zero or one;

y is zero or an integer selected from 1, 2 and 3;

$R^2$ and $R^3$ are selected independently for each occurrence from the group consisting of hydrogen and $(C_1-C_6)$ alkyl;

$R^4$ is selected from the group consisting of alkyl, alkoxy, pyranyl, benzopyranyl, pyridinyl, furanyl, cyclohexyl, aryl, substituted alkyl, substituted pyranyl, substituted benzopyranyl, substituted pyridinyl, substituted furanyl, substituted cyclohexyl, substituted aryl, and C(O) $NHR^7$; and $R^7$ is selected from the group consisting of alkyl and haloalkyl.

2. A compound according to claim 1 wherein p is equal to one.

3. A compound according to claim 1 where in p is equal to zero, q is equal to zero, and A is cyano, $CF_3$ or a halogen.

4. A compound in which p is zero and q is zero of formula II according to claim 1

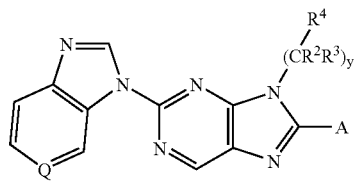

wherein
Q is selected from the group consisting of CX and nitrogen;
X is selected from the group consisting of hydrogen, halogen and an electron-withdrawing group;
A is chosen from the group consisting of alkyl, pyridinyl, pyrimidinyl, benzimidazolyl, imidazolyl, furanyl, pyrrolyl, thiazolyl, quinolinyl, morpholinyl, cyclopentyl, aryl, substituted alkyl, substituted pyridinyl, substituted pyrimidinyl, substituted benzimidazolyl, substituted imidazolyl, substituted furanyl, substituted pyrrolyl, substituted thiazolyl, substituted quinolinyl, substituted morpholinyl, substituted cyclopentyl, and substituted aryl;
y is zero or an integer selected from 1, 2 and 3;
$R^2$ and $R^3$ are selected independently for each occurrence of $(CR^2R^3)$ from the group consisting of hydrogen and $(C_1-C_6)$alkyl; and
$R^4$ is selected from the group consisting of alkyl, alkoxy, pyranyl, benzopyranyl, pyridinyl, furanyl, cyclohexyl, aryl, substituted alkyl, substituted pyranyl, substituted benzopyranyl, substituted pyridinyl, substituted furanyl, substituted cyclohexyl, and substituted aryl.

5. A compound according to claim 1 wherein Q is nitrogen of formula:

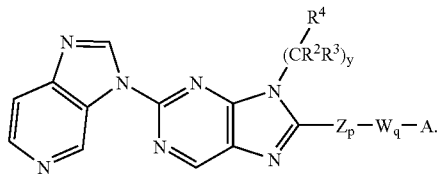

6. A compound according to claim 1 wherein Q is CX of formula:

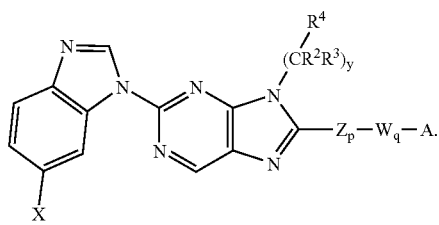

7. A compound according to claim 6 wherein X is chosen from H, F, Cl, CN, $CF_3$ and $OCF_3$.

8. A compound according to claim 1 wherein y is 1 or 2 and $R^2$ and $R^3$ are independently selected from hydrogen and methyl.

9. A compound according to claim 1 wherein y is zero and $R^4$ is a residue selected from a monocycle, a bicycle, a substituted monocycle and a substituted bicycle said residue containing at least one oxygen atom.

10. A compound according to claim 9 wherein $R^4$ is chosen from pyranyl, benzopyranyl, furanyl, optionally substituted with halogen, and a hydroxyl- or alkoxy-substituted carbocycle optionally substituted with halogen.

11. A compound according to claim 9 wherein $R^4$ is chosen from

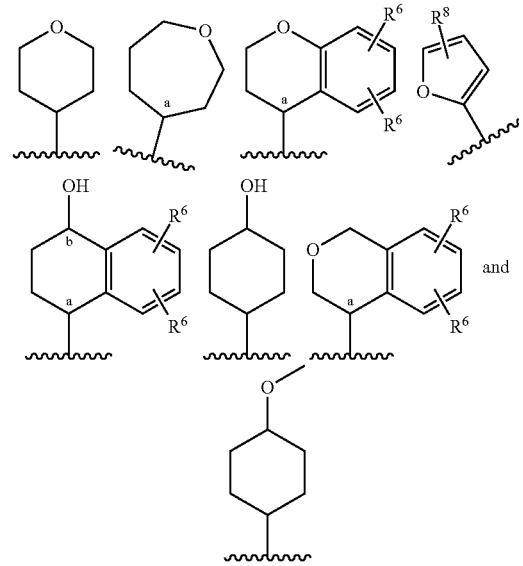

wherein $R^6$ in each occurrence is hydrogen or fluorine, $R^8$ is selected from hydrogen, lower alkyl, a halogen, and $CF_3$, and "a" and "b" represent stereogenic centers.

12. A compound according to claim 11 wherein $R^4$ is chosen from

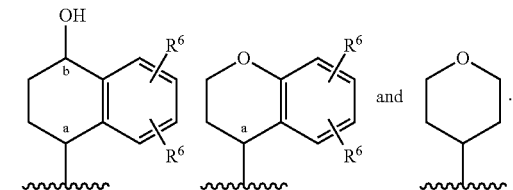

13. A compound according to claim 11 wherein the carbon marked with an "a" is of the (R)— absolute configuration.

14. A compound according to claim 13 wherein $R^4$ is

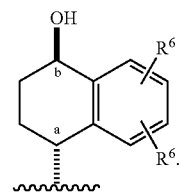

15. A compound according to claim 13 wherein $R^4$ is

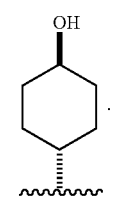

16. A compound according to claim 1 wherein $R^4$ is C(O)$NHR^7$.

17. A compound according to claim 1 wherein p and q are both zero and A is chosen from pyridinyl, pyrimidinyl, benzimidazolyl, imidazolyl, furanyl, pyrrolyl, thiazolyl, quinolinyl, morpholinyl, cyclopentyl, substituted pyridinyl, substituted pyrimidinyl, substituted benzimidazolyl, substituted imidazolyl, substituted furanyl, substituted pyrrolyl, substituted thiazolyl, substituted quinolinyl, substituted morpholinyl, substituted cyclopentyl, aryl, substituted aryl, ($C_1$-$C_6$) alkyl and substituted ($C_1$-$C_6$)alkyl.

18. A compound according to claim 17 wherein A is chosen from piperidinyl, morpholinyl, pyrimidinyl, methyl, pyridinyl, 2-aminopyrimidinyl, acetamidophenyl, propyl, hydroxyphenyl, carboxyphenyl, methanesulfonamidophenyl, halopyridinyl, methoxypyridinyl, methylpyridinyl, chloromethyl, furanyl, pyrrolyl, ethyl, butyl, imidazolyl, N-methylimidazolyl, phenyl, (aminosulfonyl)phenyl, (dialkylamino)pyrimidinyl, mono- and di-hydroxypyrimidinyl, (trifluoromethyl)pyridinyl, oxopyridinyl, (alkylthio)pyrimidinyl, (trifluoromethyl)phenyl, cyanophenyl, pyridine-N-oxide, methoxyphenyl, methylpyrrolyl, methylfuranyl, tetrahydrofuranyl, methylphenyl, cyclopentyl, thiazolyl, halophenyl, benzyl, (methoxycarbonyl)phenyl, indolyl, quinolinyl, and (trifluoromethoxy)phenyl.

19. A compound according to claim 1 wherein Z is sulfur, p is one, q is zero and A is an optionally substituted alkyl.

20. A pharmaceutical composition comprising a pharmaceutically acceptable carrier and a therapeutically effective amount of at least one compound according to claim 1.

* * * * *